(12) United States Patent
Nguyen et al.

(10) Patent No.: US 10,792,407 B2
(45) Date of Patent: Oct. 6, 2020

(54) PERCUTANEOUS DRIVELINE ANCHOR DEVICES AND METHODS OF USE

(71) Applicant: TC1 LLC, St. Paul, MN (US)

(72) Inventors: John Duc Nguyen, San Ramon, CA (US); John Donald Hill, San Francisco, CA (US); Fabian Franco, Livermore, CA (US); Chris Eskildsen, Pleasant Hill, CA (US); David Gary Eldridge, Brentwood, CA (US); Carine Hoarau, Pleasant Hill, CA (US); Yi-Ren Woo, Livermore, CA (US); John J. Hagerty, Livermore, CA (US); Pete Cardamone, Brentwood, CA (US)

(*) Notice: Subject to any disclaimer, the term of this patent is extended or adjusted under 35 U.S.C. 154(b) by 120 days.

(21) Appl. No.: 15/870,051

(22) Filed: Jan. 12, 2018

(65) Prior Publication Data
US 2018/0200422 A1    Jul. 19, 2018

Related U.S. Application Data

(60) Provisional application No. 62/445,482, filed on Jan. 12, 2017.

(51) Int. Cl.
*A61M 1/00* (2006.01)
*A61M 1/12* (2006.01)
(Continued)

(52) U.S. Cl.
CPC ............ *A61M 1/127* (2013.01); *A61M 1/122* (2014.02); *A61M 39/0247* (2013.01);
(Continued)

(58) Field of Classification Search
USPC .................................................... 600/16, 17
See application file for complete search history.

(56) References Cited

U.S. PATENT DOCUMENTS 3,663,965 A    5/1972   Lee, Jr. et al.
4,230,096 A   10/1980   Zeff et al.
(Continued)

FOREIGN PATENT DOCUMENTS

WO    03090820 A1    11/2003
WO    2009140636 A2  11/2009

OTHER PUBLICATIONS

Reichenbach et al., "Chronic Implantation of a Skeletal Muscle Energy Convertor for Cardiac Assist Devices", A Preliminary Report, ASAIO Journal 1998, 7 pages.
(Continued)

*Primary Examiner* — Nicole F Lavert
(74) *Attorney, Agent, or Firm* — Kilpatrick Townsend and Stockton LLP

(57) ABSTRACT

Systems, methods, and devices for securing a driveline to a portion of skin are disclosed herein. The driveline can connect an external controller to an implantable blood pump. The skin anchor can include a driveline capture portion. The driveline capture portion can receive the driveline and fix a position of the driveline with respect to the driveline capture portion. The driveline capture portion includes: a driveline receiver that can receive the driveline; and a driveline anchor that can engage the driveline to fix the position of the driveline with respect to the driveline receiver. The skin anchor can include a force distribution portion. The force distribution portion can engage a portion of skin and fix a position of the portion of skin with respect to the force distribution portion.

15 Claims, 13 Drawing Sheets

(51) Int. Cl.
*A61M 39/02* (2006.01)
*A61M 1/10* (2006.01)

(52) U.S. Cl.
CPC ... *A61M 1/1086* (2013.01); *A61M 2039/0261* (2013.01); *A61M 2039/0267* (2013.01); *A61M 2039/0294* (2013.01); *A61M 2205/04* (2013.01); *A61M 2205/8262* (2013.01); *A61M 2209/088* (2013.01); *A61M 2210/005* (2013.01)

(56) References Cited

U.S. PATENT DOCUMENTS

| | | |
|---|---|---|
| 4,449,975 A | 5/1984 | Perry |
| 5,224,935 A | 7/1993 | Hollands |
| 5,344,385 A | 9/1994 | Buck et al. |
| 5,395,344 A | 3/1995 | Beisang |
| 5,653,676 A | 8/1997 | Buck et al. |
| 5,695,471 A | 12/1997 | Wampler |
| 5,888,242 A | 3/1999 | Antaki et al. |
| 5,904,646 A * | 5/1999 | Jarvik ............... A61M 39/0247 600/16 |
| 6,071,093 A | 6/2000 | Hart |
| 6,116,862 A | 9/2000 | Rau et al. |
| 6,186,665 B1 | 2/2001 | Maher et al. |
| 6,234,772 B1 | 5/2001 | Wampler et al. |
| 6,264,635 B1 | 7/2001 | Wampler et al. |
| 6,572,587 B2 | 6/2003 | Lerman et al. |
| 6,688,861 B2 | 2/2004 | Wampler |
| 6,991,595 B2 | 1/2006 | Burke et al. |
| 7,361,185 B2 | 4/2008 | Omalley et al. |
| 7,686,829 B2 | 3/2010 | Elliott et al. |
| 7,699,586 B2 | 4/2010 | LaRose et al. |
| 7,927,352 B2 | 4/2011 | Wilke et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,035 B2 | 4/2012 | Earl |
| 8,152,493 B2 | 4/2012 | LaRose et al. |
| 8,323,174 B2 | 12/2012 | Jeevanandam et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,636,698 B2 | 1/2014 | Bierman et al. |
| 8,652,024 B1 | 2/2014 | Yanai et al. |
| 8,657,733 B2 | 2/2014 | Ayre et al. |
| 8,668,473 B2 | 3/2014 | LaRose et al. |
| 9,005,105 B2 | 4/2015 | Yomtov et al. |
| 9,205,230 B2 | 12/2015 | Rosenberg et al. |
| 9,242,074 B2 | 1/2016 | Olson |
| 9,242,115 B2 | 1/2016 | Freeman |
| 2005/0071001 A1 | 3/2005 | Jarvik |
| 2007/0050005 A1 | 3/2007 | Lauro |
| 2007/0078293 A1 | 4/2007 | Shambaugh, Jr. et al. |
| 2008/0021394 A1 | 1/2008 | LaRose et al. |
| 2008/0300546 A1 | 12/2008 | Godara et al. |
| 2009/0069812 A1 | 3/2009 | Gillard et al. |
| 2009/0203957 A1 | 8/2009 | LaRose et al. |
| 2010/0010449 A1 | 1/2010 | Leibowitz et al. |
| 2010/0286553 A1 | 11/2010 | Feler et al. |
| 2012/0046514 A1 | 2/2012 | Bourque |
| 2012/0046515 A1 | 2/2012 | Woo et al. |
| 2012/0095281 A1 | 4/2012 | Reichenbach et al. |
| 2012/0143297 A1 | 6/2012 | Greene |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0303020 A1 | 11/2013 | Sabin et al. |
| 2013/0314047 A1 | 11/2013 | Eagle et al. |
| 2015/0320991 A1 | 11/2015 | Sabin et al. |
| 2016/0064117 A1 | 3/2016 | Romero et al. |
| 2018/0200420 A1 | 7/2018 | Di Paola et al. |

OTHER PUBLICATIONS

Reichenbach et al., "In Vivo Studies of an Implatable Energy Convertor for Skeletal Muscle Powered Cardiac Assist", Reprinted from ASAIO Journal, Published by Lippincott-Raven Publishers, vol. 43, No. 5, © American Society for Artificial Internal Organs, Inc., Sep.-Oct. 1997, 5 pages.

* cited by examiner

PERCUTANEOUS DRIVELINE ANCHOR DEVICES AND METHODS OF USE

CROSS-REFERENCES TO RELATED APPLICATIONS

This application claims the benefit of U.S. Provisional Application No. 62/445,482, filed on Jan. 12, 2017, and entitled "PERCUTANEOUS DRIVELINE ANCHOR DEVICES AND METHODS OF USE", the entirety of which is hereby incorporated by reference herein.

BACKGROUND

This application relates generally to mechanical circulatory support systems, and more specifically relates to control systems, for an implantable blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

Due to VAD workload in constantly pumping blood, VADs can have significantly higher power requirements than other types of implantable devices such as pacemakers or other stimulators. Because of these power requirements, VADs can be externally powered by delivering power from outside of a patient's body to the VAD inside of the patient's body. In many instances, this power can be delivered via a driveline that connects to an external power source and extends into the patient's body to connect with the VAD.

One of the adverse outcomes of VAD therapy is infection. As the driveline transcutaneously extends from the external controller and/or power supply to the implanted blood pump, these infections can be located along the driveline and in many instances can be located where the driveline transcutaneously enters the body. Typically, the driveline includes a material to facilitate tissue ingrowth. In the short term the skin will heal and secure the driveline. In the longer term scar tissue forms to provide a secure stabilizing base for the driveline at the skin line. In some cases, however, the external portion of the driveline is subjected to large forces which are transferred to the skin line resulting in tearing of the tissue. If the force is large enough, the scar tissue can tear. Because scar tissue does not generally regrow over existing scar tissue, the site does not adequately heal and is subject to increased risk of infection. In more problematic cases, the infection can enter the body and subject the patient to further complications. Treating infection can be particularly difficult because CHF patients usually have difficulty healing and suffer from non-cardiac comorbidities like chronic obstructive pulmonary disease (COPD), renal failure, osteoporosis, and osteoarthritis. In some instances, such tears can require expensive and risky readmissions for surgery to properly heal and/or to clear infection, to replace the driveline, or to replace the VAD.

In addition to the risk of infection and problems associated with tearing to the regrown skin, forces applied to the driveline can result in the displacement of the driveline. This displacement can affect tissues and/or organs of the patient in which the VAD is implanted, and in instances in which the displacement is severe, could potentially damage tissues and/or organs. As a result of this, displacement of the driveline can lead to surgery to move the driveline to a desired position and/or to remedy any tissue and/or organ damage caused by the displacement.

Accordingly, there is a need for methods, systems, and devices to address these and other problems. There is a need for methods, systems, and devices to improve stabilization of the driveline. There is a need for improved methods, systems, and devices to decrease the risk of infection associated with the driveline and to decrease the risks arising from displacement and/or movement of the driveline with respect to the patients skin.

BRIEF SUMMARY

Aspects of the present disclosure relate to systems, devices, and method for reducing the risk of infection, tearing of skin surrounding and/or attaching to the driveline, and driveline displacement by anchoring the driveline. Such anchoring can result in the rigid or dynamic fixing of the driveline with respect to, for example, the skin surrounding and/or proximate to the entrance point of the driveline into the patient's body. This anchoring can be achieved via a skin anchor that can attach to and/or be affixed to the driveline and/or to a portion of skin.

Aspects of the present disclosure relate to systems, devices, and method for anchoring a driveline to a portion of skin, which portion of skin can be adjacent to and/or proximate to a port through which a driveline percutaneously enters a patient's body. The driveline can connect an external controller to an implantable blood pump, and the external controller can provide electrical power and/or control signals to the implantable blood pump. The implantable blood pump is fluidly connected to a patient's heart.

The driveline can extend from the external controller to the blood pump through the port in the patient's skin, and the driveline can be attached to a portion of the skin in the patient's body via a skin anchor. In some embodiments, this attachment to the skin can be subcutaneous and/or percutaneous. The skin anchor can include a driveline capture portion that can receive the driveline and/or a portion of the driveline and fix a position of the driveline relative to the driveline capture portion. The skin anchor can further include a force distribution portion that can engage with the skin and fix the position of the force distribution portion and/or the skin anchor with respect to the skin. In some embodiments, the driveline capture portion and the force distribution portion can be coupled to each other, and more specifically, can be statically coupled to each other. In some embodiments, the skin anchor can couple the driveline to the portion of skin such that forces applied to the driveline are transferred to the portion of skin and not to the skin directly contacting the driveline. In some embodiments, the skin anchor can couple the driveline such that a force applied to the driveline does not damage and/or tear the skin contacting the driveline and/or damage tissue connected to the implantable blood pump.

One aspect of the present disclosure relates to a skin anchor for securing a percutaneous driveline to a portion of skin. In some embodiments, the driveline can connect an external controller to an implantable blood pump. The skin anchor includes a driveline capture portion that can receive the driveline and fix a position of the driveline with respect to the driveline capture portion. In some embodiments, the driveline capture portion includes: a driveline receiver that can receive the driveline; and a driveline anchor that can engage the driveline to fix the position of the driveline with respect to the driveline receiver. The skin anchor includes a force distribution portion extending from the driveline. The force distribution portion can engage a portion of the skin and fix a position of the portion of the skin with respect to the force distribution portion.

In some embodiments, the force distribution portion comprises an enlarged member. In some embodiments, the enlarged member radially extends from the driveline when the driveline is received within the driveline capture portion. In some embodiments, the enlarged member has a diameter larger than a diameter of the driveline. In some embodiments, the driveline receiver defines an aperture that can receive the driveline. In some embodiments, the aperture has a diameter less than a diameter of the driveline. In some embodiments, the aperture includes an interior surface, and in some embodiments, the interior surface includes at least one feature that can resist displacement of the skin anchor along the driveline. In some embodiments at least one feature can be a plurality of peaks.

In some embodiments, the driveline receiver comprises a rolled sheet. In some embodiments, the force distribution portion can be a skirt radially extending around the driveline. In some embodiments, the skirt comprises a woven mesh. In some embodiments, the skirt comprises mesh formed by laser cutting. In some embodiments, the skirt can be a mesh skirt. In some embodiments, the mesh skirt can be at least one of: a silver mesh; a polymer mesh; or a titanium mesh. In some embodiments, the silver mesh can be a porous silver mesh. In some embodiments, the polymer mesh can be at least one of: polyethylene; polyethylene velour; polypropylene; polyurethane, polytetrafluoroethylene, polytetrafluoroethylene, ePTFE, polypropylene, polyester, polyethylene terephthalate, or porous silicone. In some embodiments, the polymer mesh comprises a nitinol wire mesh. In some embodiments, the mesh comprises an alloy material such as a nickel-cobalt-chromium-molybdenum alloy. In some embodiments, the mesh comprises a synthetic biocompatible material. In some embodiments, the mesh comprises a tissue material. In some embodiments, the skirt comprises two or more materials. For example, the skirt may comprise a relatively rigid metal substrate covered in a biocompatible, relatively softer material like velour or Dacron.

In some embodiments, the skirt has a diameter between 2 and 6 times greater than a diameter of the driveline. In some embodiments, the skirt can be a unitary skirt. In some embodiments, the skirt can be a two-lobe skirt. In some embodiments, the skirt can be a four-lobe skirt. In some embodiments, the skin anchor includes a tunneling bullet located intermediate between the driveline capture portion and the external controller. In some embodiments, the tunneling bullet includes a base portion and a tip portion, and in some embodiments, the base portion abuts the force distribution portion. In some embodiments, the tunneling bullet has a diameter of the base portion. In some embodiments, the diameter of the base portion is greater than the diameter of the force distribution portion.

In some embodiments, the force distribution portion can include a plurality of radially extendable tendrils. In some embodiments, each of the radially extendable tendrils can include a first arcuate component oriented in a first direction and a second arcuate component oriented in a second direction. In some embodiments, the first direction is opposite the second direction. In some embodiments, each of the radially extendable tendrils can have the first arcuate component contacting the second arcuate component.

One aspect of the present disclosure relates to a system for securing a driveline to a portion of skin via a skin anchor. In some embodiments, the driveline electrically connects an external controller and an implantable blood pump. The system includes: an implantable blood pump comprising a rotor and a stator; an external controller that can power the implantable blood pump and provide a control signal to the implantable blood pump; and a percutaneous driveline electrically connecting the implantable blood pump and the external controller. In some embodiments, the percutaneous driveline has a diameter. The system can include a skin anchor including: a driveline capture portion that can receive the driveline and fix a position of the driveline with respect to the driveline capture portion; and a force distribution portion extending from the driveline. In some embodiments, the force distribution portion can engage a portion of the skin and fix a position of the portion of the skin with respect to the force distribution portion.

In some embodiments, the force distribution portion can include an enlarged member. In some embodiments, the enlarged member radially extends from the driveline when the driveline is received within the driveline capture portion. In some embodiments, the enlarged member has a diameter larger than a diameter of the driveline. In some embodiments, the driveline receiver defines an aperture having a diameter less than a diameter of the driveline and that can receive the driveline. In some embodiments, the aperture can be an interior surface having at least one feature that can engage the driveline to fix the driveline with respect to the skin anchor. In some embodiments, the driveline receiver comprises a rolled sheet.

In some embodiments, the force distribution portion can be a skirt radially extending around the driveline. In some embodiments, the skirt can be a mesh skirt that can include at least one of: a silver mesh; a polymer mesh; or a titanium mesh. In some embodiments, the silver mesh can be a porous silver mesh. In some embodiments, the polymer mesh can include at least one of: polyethylene; polyethylene velour; polypropylene; or porous silicone. In some embodiments, the polymer mesh comprises a nitinol wire mesh. In some embodiments, the mesh comprises an alloy material such as a nickel-cobalt-chromium-molybdenum alloy. In some embodiments, the mesh comprises a synthetic biocompatible material. In some embodiments, the mesh comprises a tissue material. In some embodiments, the skirt comprises two or more materials. For example, the skirt may comprise a relatively rigid metal substrate covered in a biocompatible, relatively softer material like velour or Dacron. In some embodiments, the skirt can be a unitary skirt. In some embodiments, the skirt can be a two-lobe skirt, and in some embodiments, the skirt can be a four-lobe skirt.

In some embodiments, the system can include a tunneling bullet intermediate between the driveline capture portion and the external controller. In some embodiments, the tunneling bullet can include a base portion and a tip portion, and in some embodiments, the base portion abuts the force distribution portion. In some embodiments, the tunneling bullet can have a first diameter at the base portion. In some embodiments, the diameter of the base portion is greater than the diameter of the force distribution portion, and in some embodiments, the tunneling bullet tapers from the first diameter at the base portion to a second diameter at the tip portion. In some embodiments, the second diameter is smaller than the first diameter.

In some embodiments, the force distribution portion can include a plurality of radially deployable tendrils. In some embodiments, each of the radially deployable tendrils can include a first blade oriented in a first direction and a second blade oriented in a second direction. In some embodiments, each of the first and second blades can include a pair of ends and an arcuate component located between the pair of ends. In some embodiments, the first direction can be opposite the second direction, and in some embodiments, the arcuate component of the first blade abuts the arcuate component of the second blade.

One aspect of the present disclosure relates to a method for affixing a driveline to a portion of skin. In some embodiments, the driveline electrically connects an external controller to an implantable blood pump. The method includes: implanting the implantable blood pump in a patient's body; creating a driveline path through a patient's body; and connecting the driveline to a skin anchor via a driveline capture portion that can receive the driveline and fix a position of the driveline with respect to the driveline capture portion. In some embodiments, the driveline capture portion includes: a driveline receiver that can receive the driveline; and a driveline anchor that can engage the driveline to fix the position of the driveline with respect to the driveline receiver. The method can include: fixing the skin anchor to a portion of skin proximate to a port through which the driveline exits the patient's body via a force distribution portion extending from the driveline and that can engage a portion of the skin; and electrically connecting the external controller and the implantable blood pump.

In some embodiments, the force distribution portion can be an enlarged member radially extending from the driveline. In some embodiments, fixing the skin anchor to the portion of skin proximate to the port through which the driveline exits the patient's body can include subdermally positioning the force distribution adjacent to the portion of skin proximate to the port. In some embodiments, the enlarged member has a diameter that is larger than the port. In some embodiments, the enlarged member has a diameter larger than a diameter of the driveline.

In some embodiments, connecting the driveline to the skin anchor via the driveline capture portion includes receiving the driveline in the driveline receiver and fixing the position of the driveline with respect to the driveline receiver via the driveline anchor. In some embodiments, the driveline receiver defines an aperture comprising a diameter less than a diameter of the driveline. In some embodiments, connecting the driveline to the skin anchor includes connecting the driveline to a tunneling bullet having a first diameter at a base portion and tapering to a second diameter at a tip portion. In some embodiments, the base portion abuts the force distribution portion.

In some embodiments, creating the driveline path includes drawing the skin anchor through the patient's body such that the tunneling bullet precedes the force distribution portion through the patient's body. In some embodiments, fixing the skin anchor to a portion of skin proximate to a port through which the driveline exits the patient's body via a force distribution portion includes removing the tunneling bullet from the driveline. In some embodiments, the force distribution portion can be a disc-shaped member.

In some embodiments, the force distribution portion can be a skirt radially extending around the driveline. In some embodiments, fixing the skin anchor to a portion of skin proximate to a port through which the driveline exits the patient's body via a force distribution portion can include: positioning the force distribution portion proximate to the portion of skin; and moving the plurality of radially extendable tendrils to a deployed position. In some embodiments, moving the plurality of radially extendable tendrils to a deployed position can include redirecting first and second arcuate members through an annular ring of a stator from a longitudinal orientation to a radial orientation by centrally displacing a first slider ring connected to the first arcuate members and a second slider ring connected to the second arcuate members.

In some embodiments, the first and second arcuate members exit the annular ring in the radial orientation. In some embodiments, the first arcuate member contacts the second arcuate member when the first and second arcuate members exit the annular ring. In some embodiments, the first and second slider rings are centrally displaced by displacement of a tug connected to the first slider ring via a first tendon and connected to the second slider ring via a second tendon. In some embodiments, the first and second tendons connect to the first and second slider rings such that displacement of the tug causes equal displacement of the first and second slider rings.

The preceding presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later. For a fuller understanding of the nature and advantages of the present invention, reference should be made to the ensuing detailed description and accompanying drawings.

DETAILED DESCRIPTION

Figure 1:
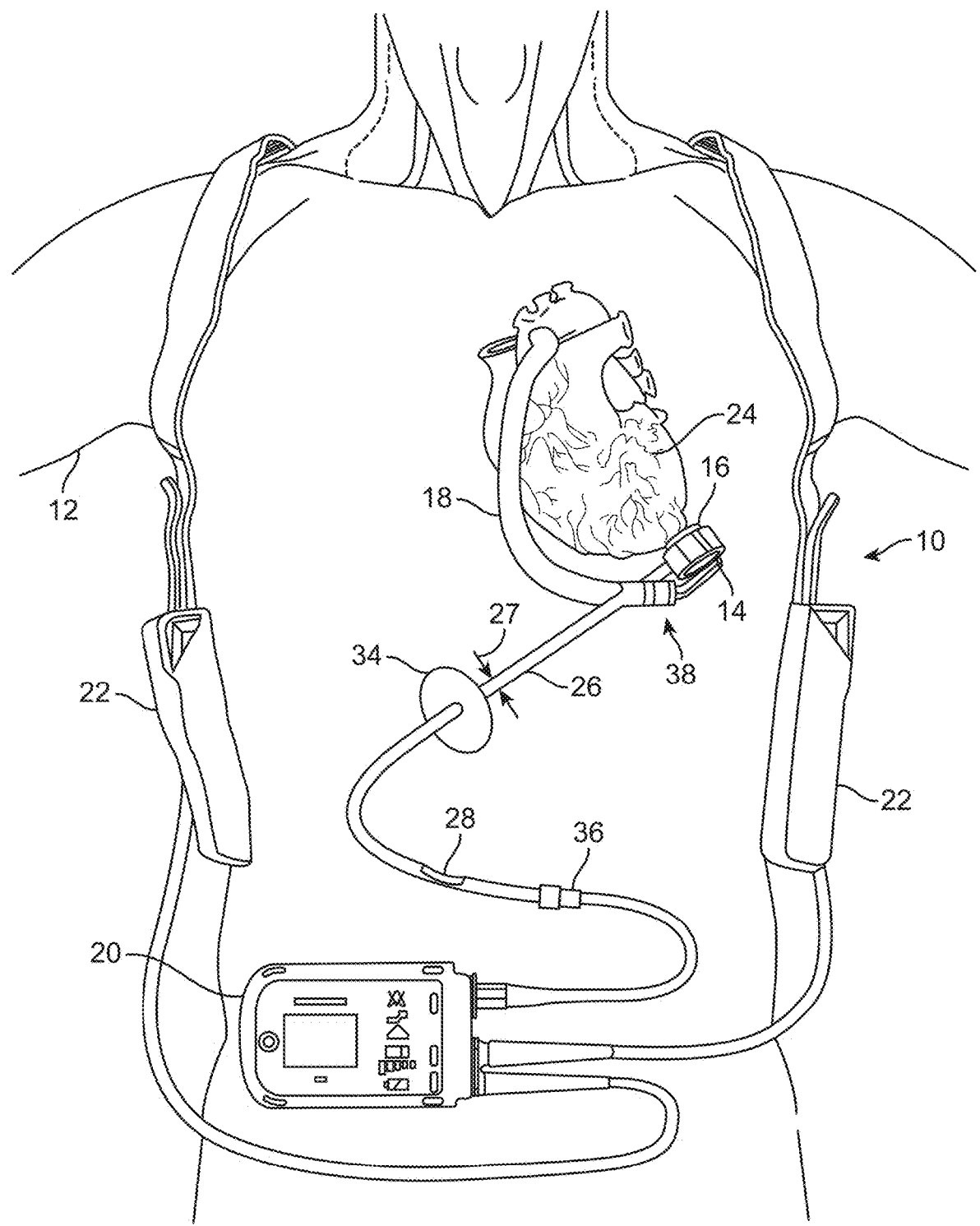
FIG. 1 is an illustration of a mechanical circulatory support system implanted in a patient's body.

A driveline of a VAD can connect the VAD to an external controller or external power source. Some embodiments of such a driveline are disclosed in U.S. Paat. No. 9,603,984, filed on Sep. 3, 2015, and entitled "TRIPLE HELIX DRIVELINE CABLE AND METHODS OF ASSEMBLY AND USE", the entirety of which is hereby incorporated by reference herein for all purposes. Such drivelines can facilitate providing the significantly higher amount of power used in operation of the VAD as compared to other types of implantable devices such as pacemakers or other stimulators. However, the driveline can cause problems as the driveline transcutaneously extends through the skin. This can increase risk of infection. Further, any movement of the driveline with respect to the patient's skin such as by the application of a force to the driveline can result in the tearing of skin and/or separation of skin from the drive, and/or can increase the risk of infection.

In addition to this, because the driveline is connected to the implantable blood pump, forces applied to the driveline can be transferred to the implantable blood pump and to the tissue and/or organ to which the implantable blood pump is connected. If sufficiently large forces are applied to the implantable blood pump via the driveline, this could result in damage to the tissue and/or organ to which the implantable blood pump is connected and/or to the separation of the implantable blood pump from that tissue and/or organ. Certain aspects of the inventions described herein are directed to reducing the risk of movement of the driveline. Various embodiments are directed to limiting movement of the driveline within a predetermined range, e.g., to mitigate the risk of tearing. The movement can be at the skin line, within the body (e.g. at the pump, or both. In various embodiments, the driveline resists any movement. A significantly higher force is applied to any movement beyond the desired and/or implant position. In various embodiments, the driveline is subjected to increased or step-change resistance outside of a proscribed range. The proscribed range may be determined by the anatomy and/or clinical context.

Some embodiments of the present disclosure address the above risks by a tissue anchor such as, for example, a skin anchor that anchors the driveline to skin and/or tissue in the patient's body, and specifically to skin and/or tissue in the patient's body that is, in some embodiments, proximate to the insertion point of the driveline. In some embodiments, these tissue anchors can comprise one or several features configured to increase the pull-out force required to pull the driveline from skin and/or damage the connection between the skin and the driveline. The skin anchor can secure the driveline to a portion of skin such as the portion of skin proximate to a port through which the driveline enters/exits the body. In some embodiments, the driveline assembly is configured as a skin button as would be understood by one of skill from the description herein. Exemplars of a skin button and related features are disclosed in U.S. Pat. Nos. 3,663,965; 4,230,096; and 9,005,105, and U.S. Patent Pub. Nos. 2013/0303020, the entire contents of which patents and publications are incorporated by reference herein for all purposes.

In some embodiments, the skin anchor can prevent, limit, and/or reduce movement of the driveline with respect to the skin that is proximate to the insertion point of the driveline. IN some embodiments, any portion of the skin anchor can serve to prevent, limit, and/or reduce movement of the driveline with respect to the skin that is proximate to the insertion point of the driveline and/or can redirect motion of the driveline and/or force applied to the driveline away from the insertion point. In some embodiments, for example, forces and/or motions applied to internal portions of the patient's body may be less damaging than forces and/or motions applied to the skin of the insertion point.

Figure 2:
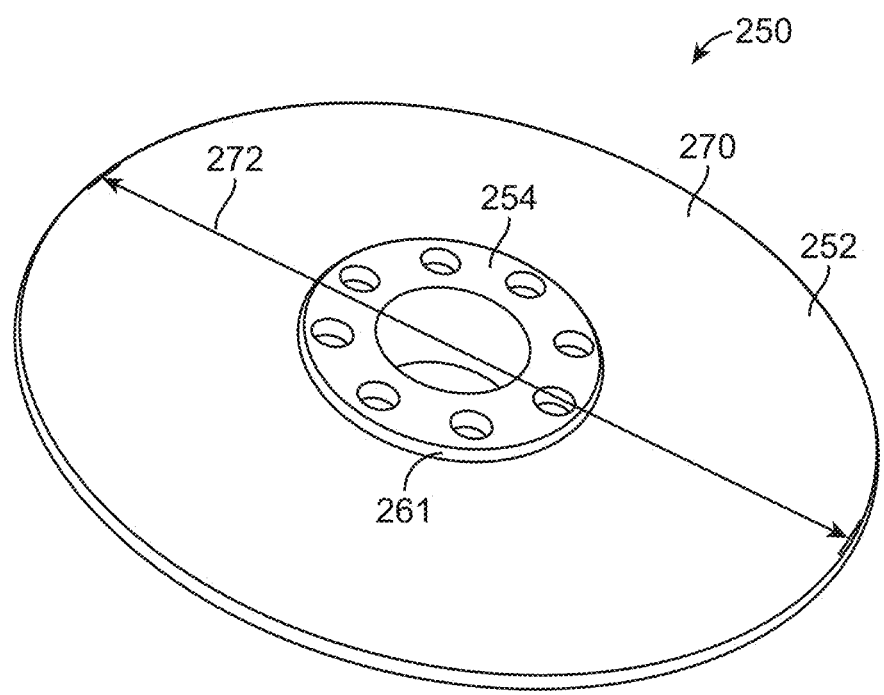
FIG. 2 is a perspective view of one embodiment of the skin anchor including a skirt.

Referring now to the drawings, in which like reference numerals represent like parts throughout the several views, FIG. 1 is an illustration of a mechanical circulatory support system 10 implanted in a patient's body 12. The mechanical circulatory support system 10 comprises an implantable blood pump 14, ventricular cuff 16, outflow cannula 18, system controller 20, and external power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, 8,668,473, 8,419,609, 7,976,271, 8,852,072, 9,091,271, 9,265,870, 8,864,643, 9,382,908, 9,068,572, and 8,882,744 all of which are incorporated herein by reference for all purposes in their entirety. With reference to FIGS. 1 and 2, the blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during external power source 22 powered operation. A driveline 26, having a diameter 27, which exits through the patient's abdomen 28, connects the implanted blood pump 14 to the system controller 20, which monitors system 10 operation. In some embodiments, the driveline 26 exits the body via a port 34 in the skin of the patient. In some embodiments, the driveline 26 can include an external connector 36 which can be located outside of the patient's body and which can separate the driveline 26 into a first piece that connects to the implanted or implantable blood pump 14 and a second piece that connects to the system controller 20. In some embodiments, the driveline 26 can connect to the implanted blood pump 14 in a hermetically sealed housing 38. In some embodiments, the driveline 26 can be a percutaneous driveline that can electrically connect the implantable blood pump 14 to the system controller 20, also referred to herein as the external controller 20. In some embodiments, the implantable blood pump 14 can include a rotor and a stator and the external controller 20 can power the implantable blood pump 14 and provide one or several control signals to the implantable blood pump 14.

Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more external power sources 22. It will be appreciated that although the system controller 20 and power source 22 are illustrated outside/external to the patient body, the driveline 26, system controller 20 and/or power source 22 may be partially or fully implantable within the patient, as separate components or integrated with the blood pump 14. Examples of such modifications are further described in U.S. Pat. No. 8,562,508 and U.S. Patent Publication No. 2013/0127253, all of which are incorporated herein by reference for all purposes in their entirety.

FIGS. 2 through 8 relate to embodiments of a skin anchor including a skirt. With reference now to FIG. 2, a perspective view of one embodiment of a skin anchor 250 including a skirt 252 is shown. The skin anchor 250 includes a driveline capture portion 254. The driveline capture portion 254 can comprise a variety of shapes and sizes and can be made from a variety of materials. In some embodiments, the driveline capture portion 254 is configured to receive the driveline 26 and fix a position of the driveline 26 with respect to the driveline capture portion 254. As used herein, fixing the position of the driveline can refer to limiting motion entirely or within a proscribed range. In various respects, fixing and anchoring are used somewhat interchangeably.

The driveline capture portion 254 includes a driveline receiver 256 that receives the driveline 26 and a driveline anchor 258 that engages the driveline 26 to fix the position of the driveline 26 with respect to the driveline anchor 258, the driveline receiver 256, and/or the driveline capture portion 254. In some embodiments, the driveline receiver 256 can define a feature such as a channel or aperture that can receive the driveline 26. As specifically shown in FIG. 3, in some embodiments, the driveline receiver 256 defines an aperture 260 can be, for example, a circular or cylindrical aperture. In some embodiments, the aperture 260 can have a diameter 262. The diameter 262 can be sized with respect to a diameter 27 of the driveline 26 such that the driveline 26 can be received within the aperture 260.

In some embodiments, the diameter 262 of the aperture 260 can be greater than the diameter 27 of the driveline 26, can be equal to the diameter 27 of the driveline 26, or can be less than the diameter 27 of the driveline 26. In some embodiments, the diameter 262 of the aperture 260 can be selected so as to create a friction fit between the driveline 26 and the inner surface 264 of the aperture 260. In some embodiments, this can result in the elastic deformation of all or portions of the driveline receiver 256 and/or the driveline 26 when the driveline 26 is inserted into and/or through the aperture 260.

In some embodiments, the diameter 262 of the aperture 260 can be selected so that an inner surface 264 of the aperture 260, which inner surface can be the driveline anchor 258, engages with the driveline 26 to secure the position of the driveline 26 with respect to the aperture 260. In some embodiments, this inner surface 264 of the aperture 260 can comprise one or several features and/or materials that interact with the driveline 26 to prevent, limit, and/or reduce movement of the driveline 26 with respect to the aperture 260. In some embodiments, these one or several features of the inner surface 264 can include, for example, a textured surface, a pitted surface, one or several ribs or peaks, one or several grooves, or other mechanical features as would be understood by one of skill from the description herein. In some embodiments, these materials can include a high friction material, adhesive, is sticky and/or tacky material, rubber, or a deformable material.

Figure 3:
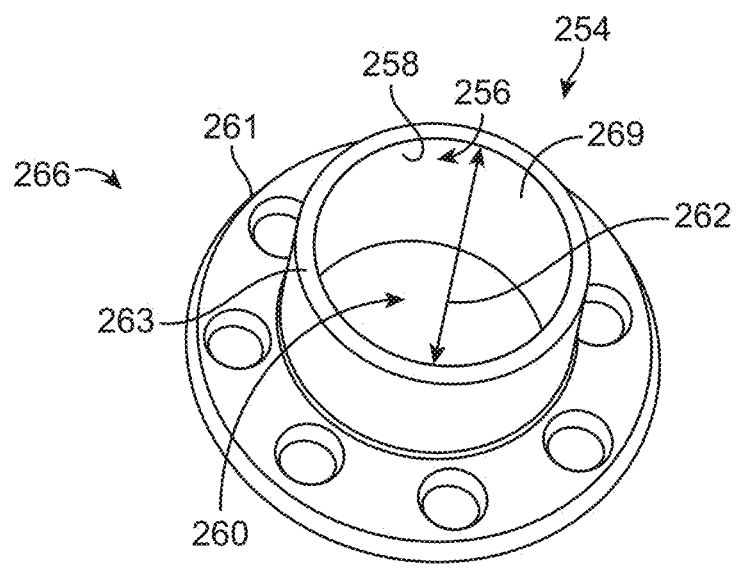
FIG. 3 is a perspective view of one embodiment of a driveline receiver.
Figure 4:
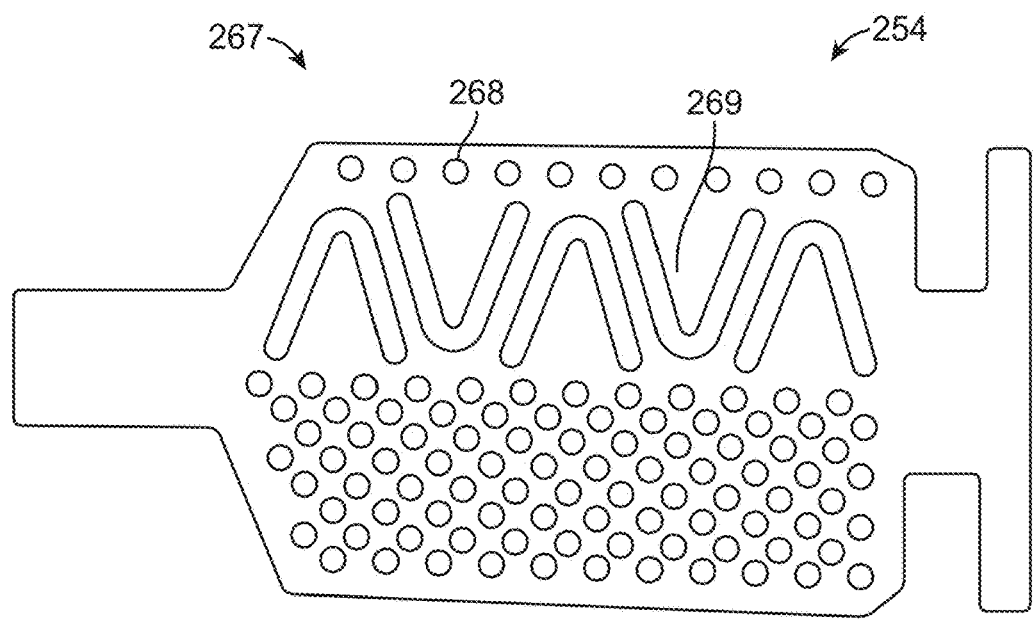
FIG. 4 is a front view of one embodiment of a sheet member that can be used in creating a driveline receiver.
Figure 5:
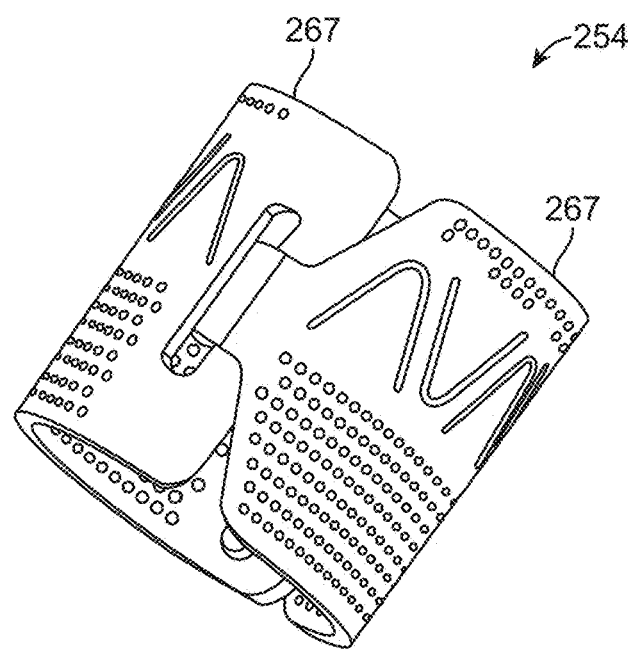
FIG. 5 is a perspective view of one embodiment of a driveline receiver created by at least one sheet member.

Embodiments of the driveline capture portion 254 are depicted in FIGS. 3 through 5. In some embodiments, the driveline capture portion 254 can comprise an annular member 266 as depicted in FIG. 3. In such an embodiment, the annular member 266 can comprise a flange 261 extending from a tubular member 263. In some embodiments, the flange 261 can comprise a mounting flange. In some embodiments, the driveline capture portion 254 can comprise one or several sheet members 267 that can be in a planar configuration as depicted in FIG. 4 or in a rolled configuration as depicted in FIG. 5. Thus, in some embodiments, the driveline capture portion 254 and/or the driveline receiver 256 can comprise at least one rolled sheet member 267. In the specific embodiment depicted in FIG. 5, the driveline capture portion 254 and/or the driveline receiver 256 comprises two connected, rolled sheet members 267.

Figure 6:
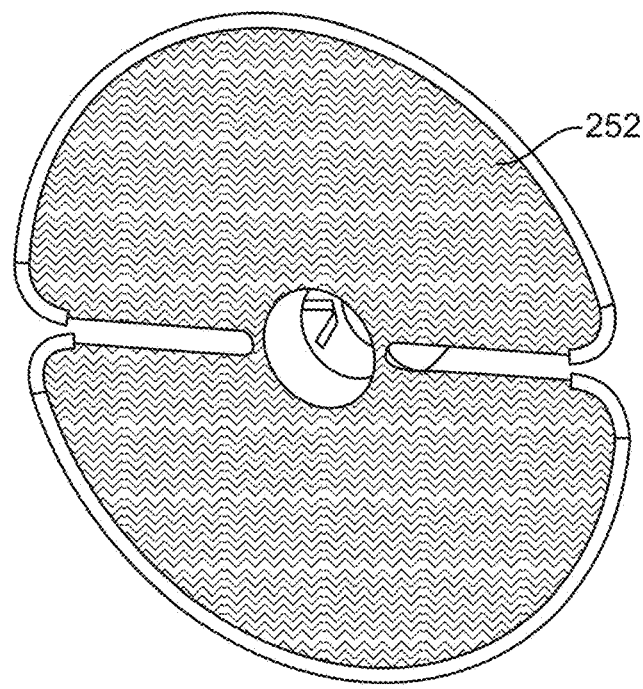
FIG. 6 is a perspective view of a two-lobbed skirt.

As depicted in FIGS. 5 and 6, the sheet member 267 can include features configured to facilitate engagement with the driveline 26 and/or with the force distribution portion 270. In some embodiments, this can include a plurality of first features 268 and a plurality of second features 269. In some embodiments, the first features 268 can comprise a plurality of raised conically shaped elements created by punching through the sheet member 267. In some embodiments, the second features 269 can comprise one or several foldable tabs that can be folded to create a channel for retaining the force distribution portion 270 is a desired location on the driveline capture portion 254.

The skin anchor 250 can include a force distribution portion 270 that can comprise, for example, an enlarged member. In some embodiments, the enlarged member can radially extend from the driveline 26 when the driveline 26 is received within the driveline capture portion 254. In some embodiments, the diameter of the enlarged member can be larger than the diameter of the driveline. The force distribution portion 270 can comprise a variety of shapes and sizes and can be made from a variety of materials. In some embodiments, the force distribution portion 270 extends from the driveline capture portion 254 and can be configured to engage a portion of skin to fix a position of the portion of skin with respect to, for example, the skin anchor 250, the force distribution portion 270, and/or the driveline capture portion 254. In some embodiments, the portion of the skin engaged by the force distribution portion 270 can be proximate to the port 34.

Figure 7:
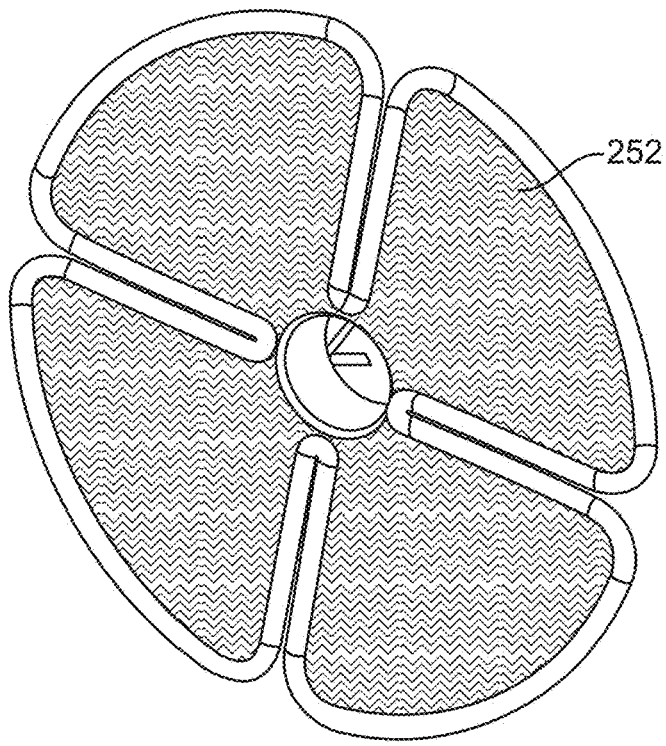
FIG. 7 is a perspective view of a four-lobbed skirt.
Figure 20:
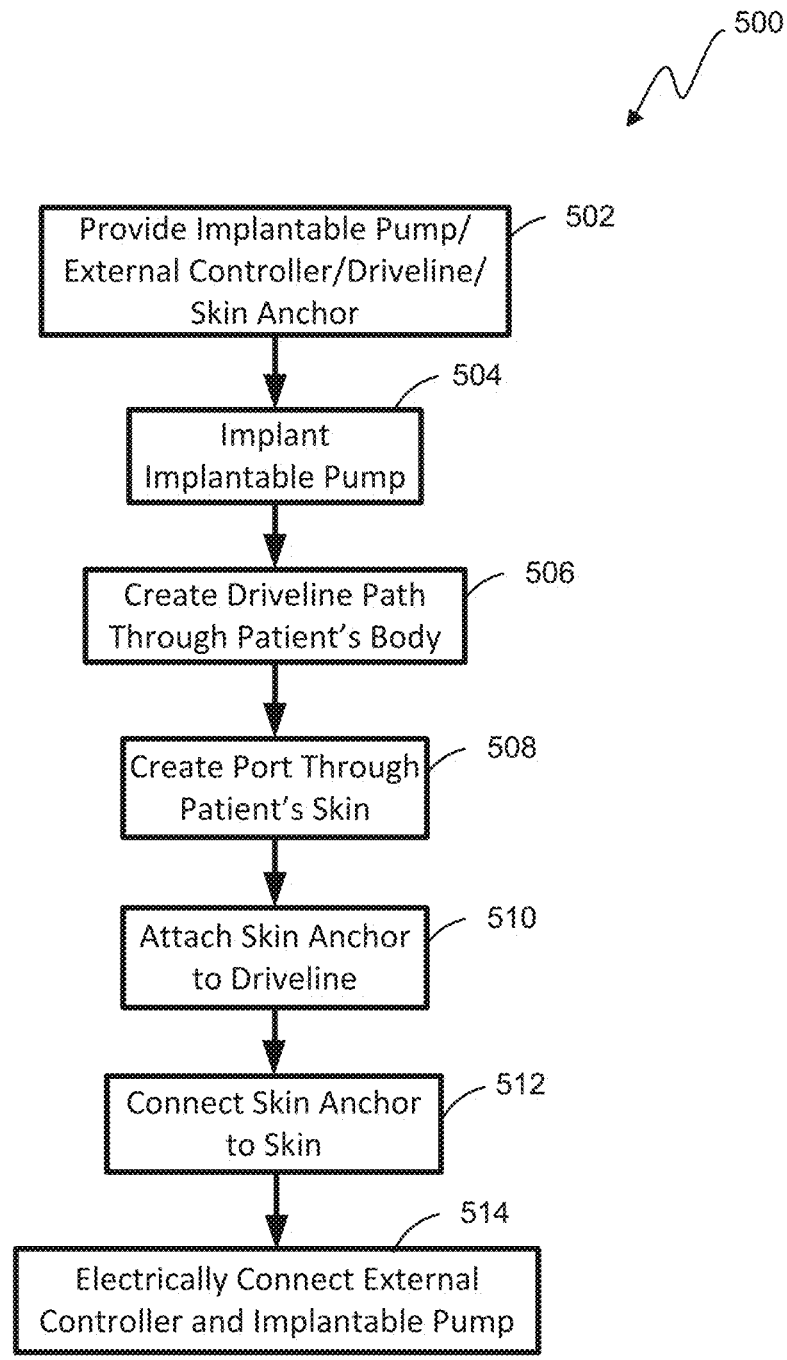
FIG. 20 is a flowchart illustrating one embodiment of a process for affixing a driveline to a portion of skin.

In some embodiments, the force distribution portion 270 can comprise the skirt 252 which can attach to the driveline capture portion 254 and/or extend around all or portions of the driveline capture portion 254 and/or the driveline 26. In some embodiments, the skirt 252 can attach to the driveline capture portion 254 and radially extend around all or portions of the driveline capture portion 254 and/or the driveline 26. The skirt 252 can comprise a variety of shapes and sizes and can be made of a variety of materials. In some embodiments, and as shown in FIG. 20, the skirt comprises a disc-shaped annular member that can centrally receive the driveline capture portion 254 as depicted in FIG. 2. In some embodiments, the skirt 252 can be received on the driveline capture portion 254 such that the skirt abuts the flange 261. The skirt 252 can comprise a unitary skirt as shown in FIG. 2, a two-lobe skirt 252 as shown in FIG. 6, a four-lobe skirt 252 as shown in FIG. 7, or can have any other desired number of lobes.

The skirt 252 can comprise a variety of materials. In some embodiments, for example, the skirt 252 can be made from one or several metals or alloys such as, for example: silver; stainless steel; titanium; or any bio-compatible metal. In some embodiments, the skirt 252 can be made from one or several polymers such as, for example: polyethylene; polypropylene, silicone, or any bio-compatible polymer. In some embodiments, the skirt 252 can comprise a mesh and/or can be porous. In some embodiments, for example, the mesh skirt can comprise at least one of: a silver mesh, including porous silver; a polymer mesh; or a titanium mesh. In some embodiments, the polymer mesh comprises at least one of: polyethylene; polyethylene velour; polypropylene; or porous silicone.

The skirt 252 can comprise a variety of shapes and sizes. In some embodiments, the skirt 252 can be circular, rectangular, triangular, or can have any other desired shape. In some embodiments, the skirt can have a diameter 272 that is greater than the diameter 27 of the driveline 26 and/or that is greater than the diameter 262 of the aperture 260 of the driveline capture portion 254. In some embodiments, the diameter 272 of the skirt 252 can be: between 2 and 20 times greater than the diameter 27 of the driveline 26 and/or that is greater than the diameter 262 of the aperture 260 of the driveline capture portion 254; between 2 and 15 times greater than the diameter 27 of the driveline 26 and/or that is greater than the diameter 262 of the aperture 260 of the driveline capture portion 254; between 2 and 10 times greater than the diameter 27 of the driveline 26 and/or that is greater than the diameter 262 of the aperture 260 of the driveline capture portion 254; between 2 and 6 times greater than the diameter 27 of the driveline 26 and/or that is greater than the diameter 262 of the aperture 260 of the driveline capture portion 254; between 2 and 4 times greater than the diameter 27 of the driveline 26 and/or that is greater than the diameter 262 of the aperture 260 of the driveline capture portion 254; and/or any between any other or intermediate ratios of the diameter 27 of the driveline 26 and/or that is greater than the diameter 262 of the aperture 260 of the driveline capture portion 254.

Figure 8:
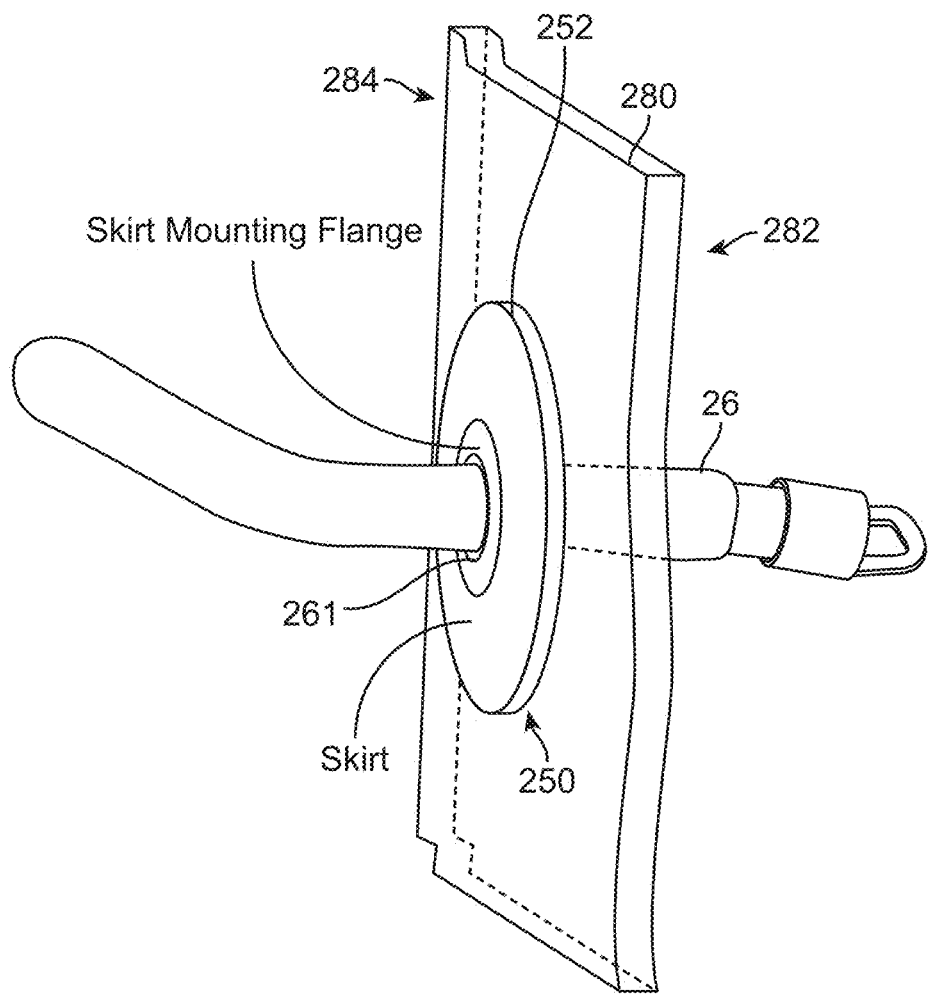
FIG. 8 is a perspective view of one embodiment of a skin anchor in a deployed configuration.

FIG. 8 depicts on embodiment of the skin anchor 250 in a deployed, subdermal configuration. As seen in FIG. 8, the driveline 26 passes through the skin 280 from an external side 282 of the skin 280 to an internal side 284 of the skin. The skin anchor 250 is connected to the driveline and is positioned such that the force distribution portion 270, and specifically the skirt 252 is adjacent to the internal side 284 of the skin 280, and specifically abuts the internal side 284 of the skin 280. In some embodiments, the skin anchor is configured for implantation subcutaneously. In some embodiments, the skin anchor is configured for implantation subdermally or within the skin layers. In some embodiments, the skin anchor is configured for implantation deeper within the body and below the skin. In some embodiments, the skin anchor 250 can be positioned such that the skirt 252 is positioned between the flange 261 and the internal side 284 of the skin 280. In some embodiments, the force distribution portion 270 can have a diameter that is larger than a diameter of the driveline 26 and/or the force distribution portion 270 and/or a diameter of the force distribution portion can be larger than the port 34. In some embodiments, this positioning of the skin anchor 250 can prevent the pulling-out of the skin anchor 250 from the skin 280.

Figure 9:
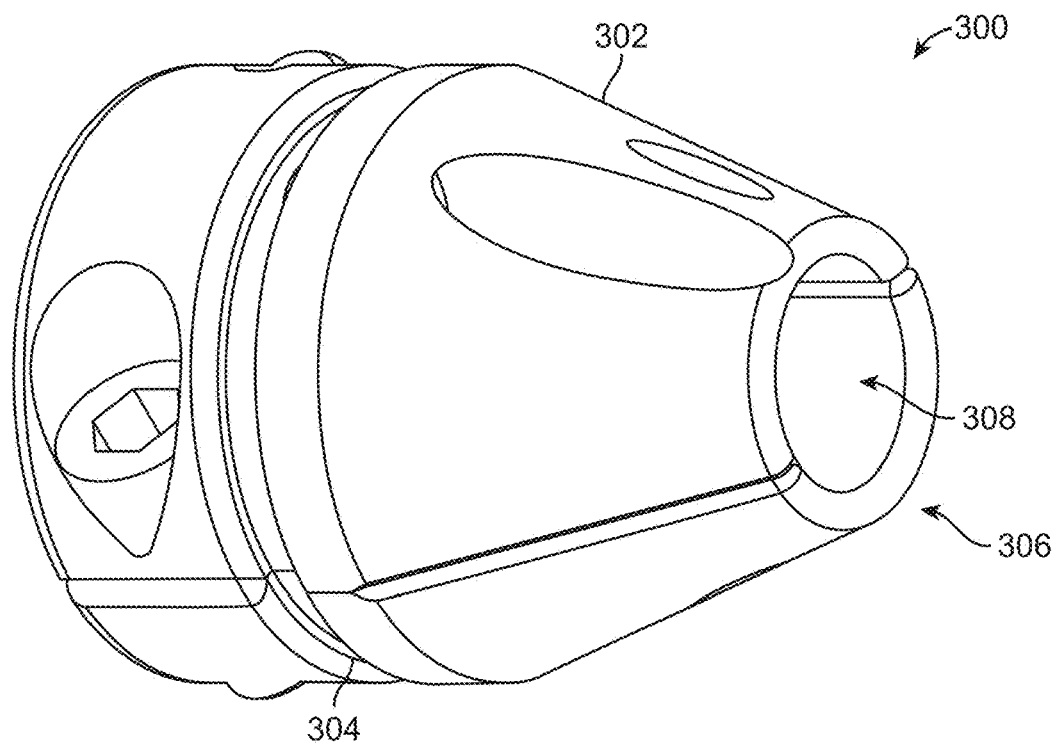
FIG. 9 is a perspective view of one embodiment of a skin anchor including a tunneling bullet.
Figure 10:
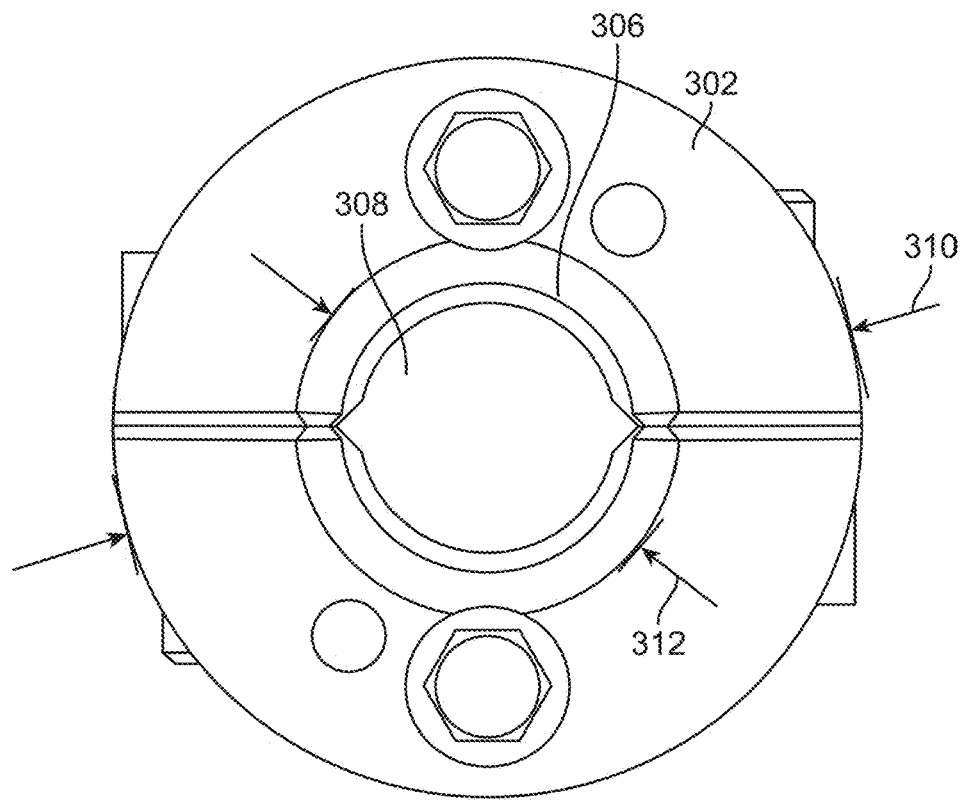
FIG. 10 is a front view of one embodiment of the skin anchor including the tunneling bullet.
Figure 11:
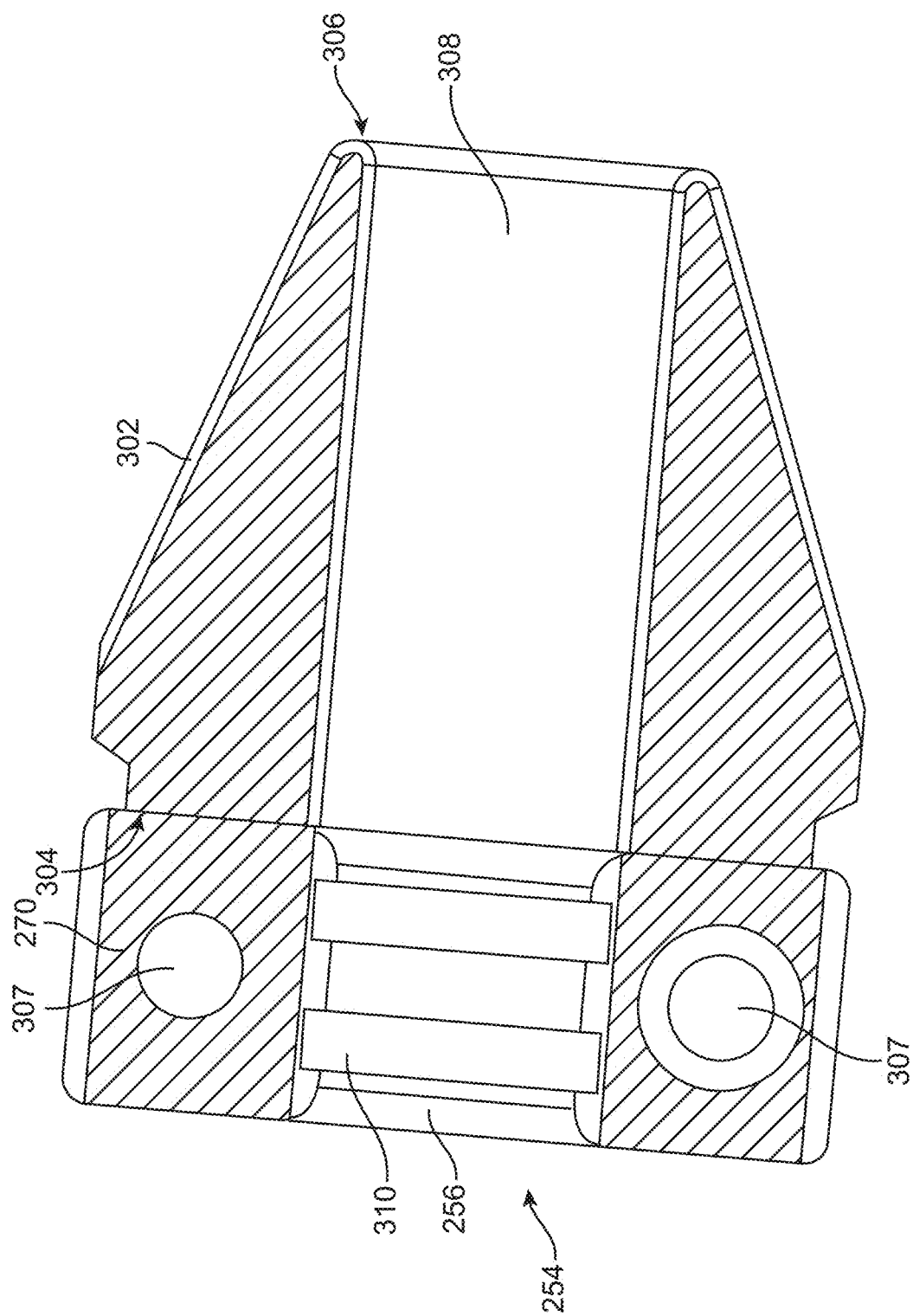
FIG. 11 is a section view of one embodiment of the skin anchor including the tunneling bullet.

With reference now to FIGS. 9 through 15, views of embodiments of a skin anchor 300 with a tunneling bullet 302 are shown. In these, FIG. 9 is a perspective view of the skin anchor 300, FIG. 10 is a front view of the skin anchor 300, and FIG. 11 is a section view of the skin anchor 300. As seen in FIG. 9, the tunneling bullet 302 can comprise a base portion 304 and a tip 306 and an aperture 308 extending from the base 304 to the tip 306. As seen in the front view shown in FIG. 10, the base 304 can comprise a first diameter 310 and the tip 306 can comprise a second diameter 312. In the depicted embodiment, the first diameter 310 is larger than the second diameter 312, and thus the tunneling bullet 302 tapers from the first diameter 310 to the second diameter 312 giving the tunneling bullet 302, in some embodiments, the shape of a truncated cone.

The skin anchor 300 includes base portion 301 that can include a first piece 303 and a second piece 305. In some embodiments, the first and second pieces 303, 305 can be connected to each other. In some embodiments, the first and second pieces 303, 305 can be connected by one or several features, adhesives, fasteners, or other mechanical features as would be understood by one of skill from the description herein. In some embodiments, these one or several fasteners can include one or several screws extending through screw holes 307.

The skin anchor 300 can include a driveline capture portion 254 configured to receive the driveline 26 and fix a position of the driveline 26 with respect to the driveline capture portion 254. The driveline capture portion 254 can comprise a variety of shapes and sizes and can be made from a variety of materials depending on the application as will be understood by one of skill from the description herein. In some embodiments, the driveline capture portion 254 is configured to receive the driveline 26 and fix a position of the driveline 26 with respect to the driveline capture portion 254.

The driveline capture portion 254 includes a driveline receiver 256 that receives the driveline 26 and a driveline anchor 258 that engages the driveline 26 to fix the position of the driveline 26 with respect to the driveline anchor 258, the driveline receiver 256, and/or the driveline capture portion 254. In some embodiments, the driveline receiver 256 can define a feature such as a channel or aperture that can receive the driveline 26. As specifically shown in FIG. 3, in some embodiments, the driveline receiver 256 defines an aperture 260 can be, for example, a circular or cylindrical aperture. In some embodiments, the aperture 260 can be formed by the connection of the first piece 303 to the second piece 305. In some embodiments, for example, the first piece 303 can be positioned on one side of the driveline 26 and the second piece can be positioned on the other side of the driveline 26, and the first and second pieces 303, 305 can then be connected via screws extending through the screw holes 307 to capture the driveline 26 within the aperture 260.

Figure 12:
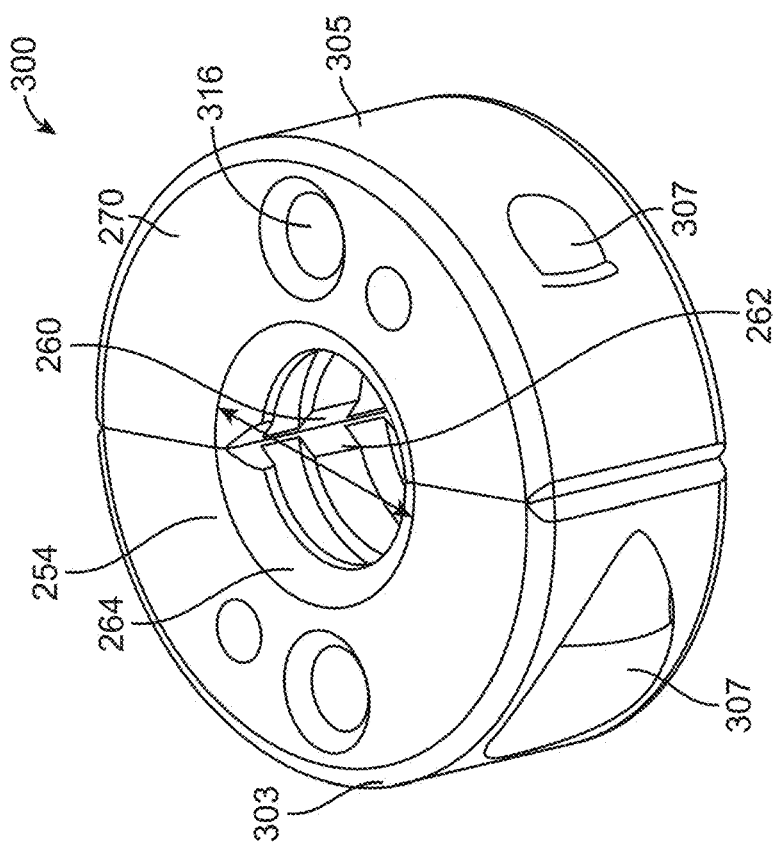
FIG. 12 is a perspective view of one embodiment of a base portion of a skin anchor.
Figure 14:
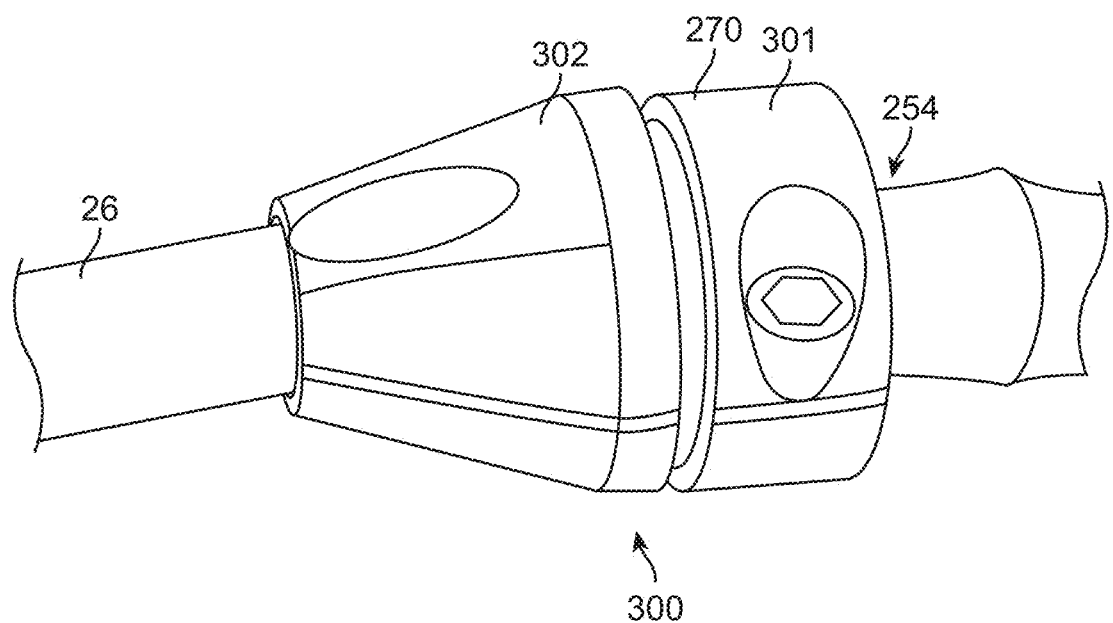
FIG. 14 is a perspective view of one embodiment of a skin anchor including the tunneling bullet and the driveline.

In some embodiments, and as seen in FIG. 12, the aperture 260 can have a diameter 262. The diameter 262 can be sized with respect to a diameter 27 of the driveline 26 such that the driveline 26 can be received within the aperture 260. In some embodiments, the diameter 262 of the aperture 260 can be greater than the diameter 27 of the driveline 26, can be equal to the diameter 27 of the driveline 26, or can be less than the diameter 27 of the driveline 26. In some embodiments, the diameter 262 of the aperture 260 can be selected so as to create a friction fit between the driveline 26 and the inner surface 264 of the aperture 260. In some embodiments, this can result in the elastic deformation of all or portions of the driveline receiver 256 and/or the driveline 26 when the driveline 26 is inserted into and/or through the aperture 260.

In some embodiments, the diameter 262 of the aperture 260 can be selected so that an inner surface 264 of the aperture 260, which inner surface can be the driveline anchor 258, engages with the driveline 26 to secure the position of the driveline 26 with respect to the aperture 260. In some embodiments, this inner surface 264 of the aperture 260 can comprise one or several features 310 and/or materials that interact with the driveline 26 to prevent movement of the driveline 26 with respect to the aperture 260. In some embodiments, these one or several features of the inner surface 264 can include, for example, a textured surface, a pitted surface, one or several ribs or peaks, one or several grooves, or other mechanical features as would be understood by one of skill from the description herein. In some embodiments, these materials can include a high friction material, adhesive, is sticky and/or tacky material, rubber, or a deformable material.

The skin anchor 300 can include a force distribution portion 270 that can comprise, for example, an enlarged member. In some embodiments, the enlarged member can radially extend from the driveline 26 when the driveline 26 is received within the driveline capture portion 254. In some embodiments, the diameter of the enlarged member can be larger than the diameter of the driveline 26.

The force distribution portion 270 can comprise a variety of shapes and sizes and can be made from a variety of materials. In some embodiments, the force distribution portion 270 extends from the driveline capture portion 254 and can be configured to engage a portion of skin to fix a position of the portion of skin with respect to, for example, the skin anchor 300, the force distribution portion 270, and/or the driveline capture portion 254. In some embodiments, the portion of the skin engaged by the force distribution portion 270 can be proximate to the port 34.

Figure 13:
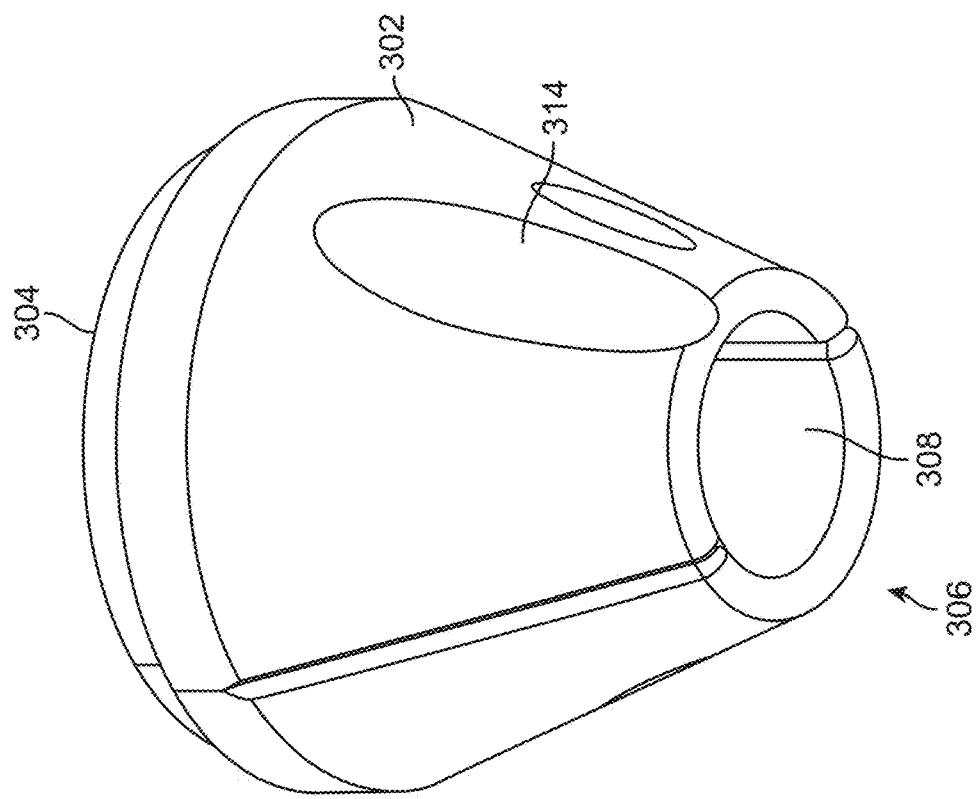
FIG. 13 is a perspective view of one embodiment of a tunneling bullet.

In some embodiments, and as shown in FIG. 11, the base 304 of the tunneling bullet 302 can abut the force distribution portion 270 of the skin anchor 300. In some embodiments, base 304 of the tunneling bullet 302 can abut the force distribution portion 270 of the skin anchor 300 such that the aperture 308 of the tunneling bullet 302 aligns with the aperture 260 of the driveline capture portion 254 such that the driveline 26 can be received through both of the apertures 260, 308 as shown in the perspective view of the skin anchor 300 in FIG. 14. In some embodiments, the tunneling bullet 302 can be connected to the force distribution portion 270. In some embodiments, the tunneling bullet 302 can be connected to the force distribution portion 270 can be connected by one or several features, adhesives, fasteners, or other mechanical features as would be understood by one of skill from the description herein. In some embodiments, these one or several fasteners can include one or several screws that extend through one or several screw holes 314, as shown in FIG. 13, in the tunneling bullet 302 and into one or several screw holes 316 in the force distribution portion 270.

In some embodiments, the skin anchor 300 can be connected to the driveline 26 by connecting the first and second pieces 303, 305 of the base portion 301 around and to the driveline 26. The screws connecting the first and second pieces 303, 305 can be tightened such that the position of the skin anchor 300 along the driveline 26 is secured. The tunneling bullet 302 can be connected to the base portion 301 and the skin anchor 300 can be used in creating a driveline path through all or portions of the patient's body. In some embodiments, the creation of the driveline path can include drawing the skin anchor 300 through the patient's body such that the tunneling bullet 302 precedes the base portion 301 and the thereto coupled force distribution portion 270 through the patient's body. In such an embodiment, the tunneling bullet 302 can be positioned intermediate between the base portion 301 and the port 34 and/or the external controller 20.

Figure 15:
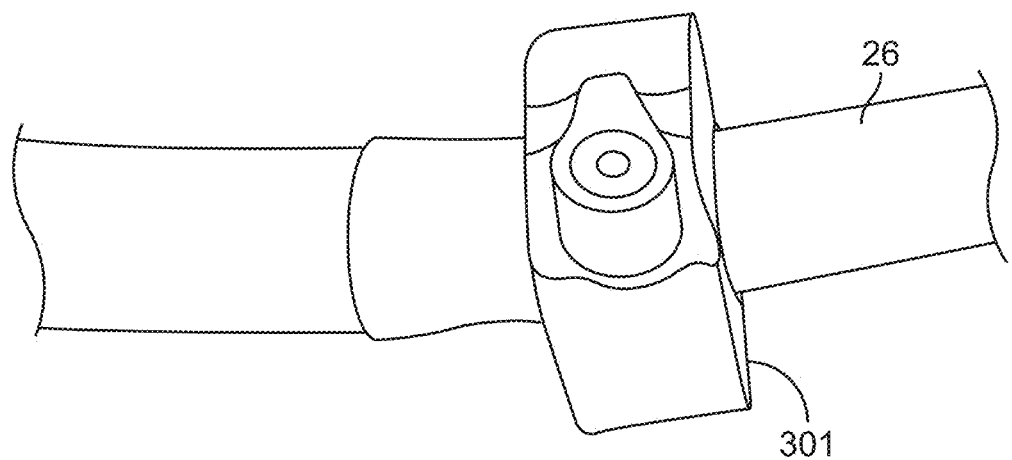
FIG. 15 is a perspective view of one embodiment of the base portion of the skin anchor and the driveline.

In some embodiments, the tunneling bullet 302 can be sized and shaped such that the tunneling bullet 302 elastically deforms the tissue through which it is drawn to thereby create a temporary cavity in the tissue through which the base portion 301 and the thereto coupled force distribution portion 270 can pass. When the skin anchor 300 reaches the desired location, the tunneling bullet 302 can be removed from the base portion 301 and the base portion 301 can be positioned, for example, proximate to the skin surrounding the port 34. The removal of the tunneling bullet 302 from the skin anchor 300 can leave the base portion 301 attached to the driveline 26 as shown in FIG. 15. In such an embodiment, removing the tunneling bullet 302 from the driveline 26 can fix the skin anchor 300 to the portion of skin surrounding and/or proximate to the port 34.

Figure 16:
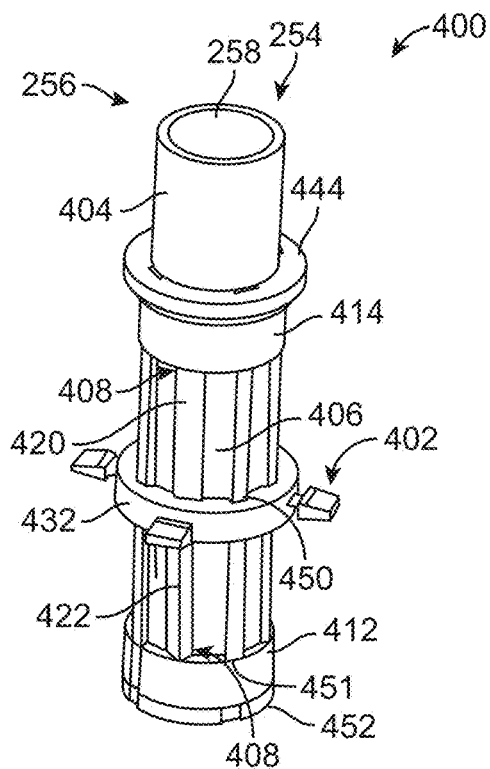
FIG. 16 is a perspective view of one embodiment of a skin anchor including deployable tendrils in an undeployed configuration.

FIGS. 16 through 19 show an embodiment of the skin anchor 400 with deployable tendrils 402. In FIG. 16, a perspective view of the skin anchor 400 is shown with the tendrils 402 in an undeployed configuration, and in FIG. 17, the skin anchor 400 is shown with the tendrils 402 in a deployed configuration. The skin anchor 400 can include a driveline capture portion 254 that can be a stator 404. The driveline capture portion 254 can be configured to receive the driveline 26 and fix a position of the driveline 26 with respect to the driveline capture portion 254. The driveline capture portion 254 can comprise a variety of shapes and sizes and can be made from a variety of materials. In some embodiments, the driveline capture portion 254 is configured to receive the driveline 26 and fix a position of the driveline 26 with respect to the driveline capture portion 254.

The driveline capture portion 254 includes a driveline receiver 256 that receives the driveline 26 and a driveline anchor 258 that engages the driveline 26 to fix the position of the driveline 26 with respect to the driveline anchor 258, the driveline receiver 256, and/or the driveline capture portion 254. In some embodiments, the driveline receiver 256 can define a feature such as a channel or aperture that can receive the driveline 26. As specifically shown in FIGS. 16 and 17, in some embodiments, the driveline receiver 256 defines an aperture 260 can be, for example, a circular or cylindrical aperture. In some embodiments, the aperture 260 can be formed in the stator 404, and can particularly, longitudinally extend through the stator 404.

In some embodiments, the aperture 260 can have a diameter 262. The diameter 262 can be sized with respect to a diameter 27 of the driveline 26 such that the driveline 26 can be received within the aperture 260. In some embodiments, the diameter 262 of the aperture 260 can be greater than the diameter 27 of the driveline 26, can be equal to the diameter 27 of the driveline 26, or can be less than the diameter 27 of the driveline 26. In some embodiments, the diameter 262 of the aperture 260 can be selected so as to create a friction fit between the driveline 26 and the inner surface 264 of the aperture 260. In some embodiments, this can result in the elastic deformation of all or portions of the driveline receiver 256 and/or the driveline 26 when the driveline 26 is inserted into and/or through the aperture 260.

In some embodiments, the diameter 262 of the aperture 260 can be selected so that an inner surface 264 of the aperture 260, which inner surface can be the driveline anchor 258, engages with the driveline 26 to secure the position of the driveline 26 with respect to the aperture 260. In some embodiments, this inner surface 264 of the aperture 260 can comprise one or several features 406 and/or materials that interact with the driveline 26 to prevent movement of the driveline 26 with respect to the aperture 260. In some embodiments, these one or several features of the inner surface 264 can include, for example, bendable tabs that can be forced onto the driveline 26 to engage with the driveline, a textured surface, a pitted surface, one or several ribs or peaks, one or several grooves, other mechanical features as would be understood by one of skill from the description herein. In some embodiments, these materials can include a high friction material, adhesive, is sticky and/or tacky material, rubber, or a deformable material.

The skin anchor 400 can include a force distribution portion 270 that can comprise a plurality of tendrils 402 that can be, for example, radially extendable. In some embodiments, the force distribution portion 270 can be configured to secure the skin anchor 400 to a portion of skin proximate to the port 34 so as to minimize damage to the skin surrounding the port 34 due to loads applied to the driveline 26. In some embodiments, tendrils 402 can be moved from the undeployed configuration shown in FIG. 16 to the deployed configuration shown in FIG. 17. The tendrils 402 can comprise a first end 408 and a second end 410. The first end 408 of the tendrils 402 can connect to an inward ring 412, also referred to herein as a first slider ring 412, and/or an outward ring 414, also referred to herein as a second slider ring 414, and the second ends 410 can connect to a fluke 416.

In some embodiments, the tendrils 402 in a deployed configuration define an enlarged member that can, for example, radially extend from the driveline 26 when the driveline 26 is received within the driveline capture portion 254. In some embodiments, the diameter of the enlarged member, which can comprise the diameter of a circle 418 defined by the radially outermost points of the flukes 416 of the tendrils 402 can be larger than the diameter of the driveline 26.

In some embodiments, each of the tendrils 402 can be formed by a first blade 420 and a second blade 422. In some embodiments, the first blade 420 can connect to the outward ring 414 at the first end 408 of the first blade 420 and the second blade 422 can connect to the inward ring 412 at the first end 408 of the second blade 420. In some embodiments, the second ends 410 of each of the first and second blades 420, 422 can connect to the fluke 416.

The blades 420, 422 can comprise a variety of shapes and sizes and can be made from a variety of materials. In some embodiments, each of the blades 420, 422 can comprise an elongate member extending from the first end 408 to the second end 410 and a longitudinal axis extending between the first and second ends 408, 410. In some embodiments, the blades 420, 422 can be flexible and/or bendable in one direction perpendicular to the longitudinal axis at the location of the bending. In some embodiments, the first and second blades 420, 422 can be flexible in opposite directions perpendicular to the longitudinal axis such that when the blades 420, 422 are adjacent in the deployed configuration of the tendril 402, the tendril is non-flexible.

Figure 17:
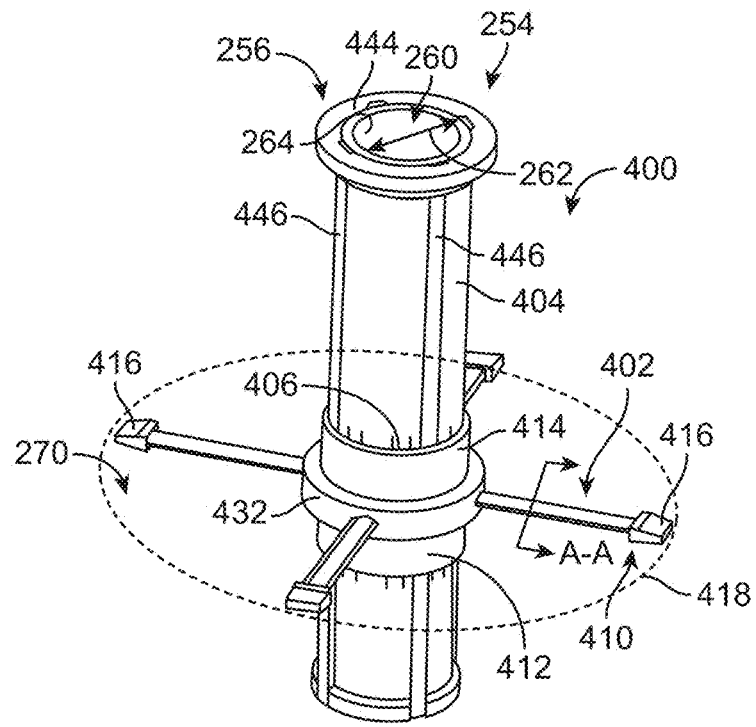
FIG. 17 is a perspective view of one embodiment of a skin anchor including deployable tendrils in a deployed configuration.
Figure 18:
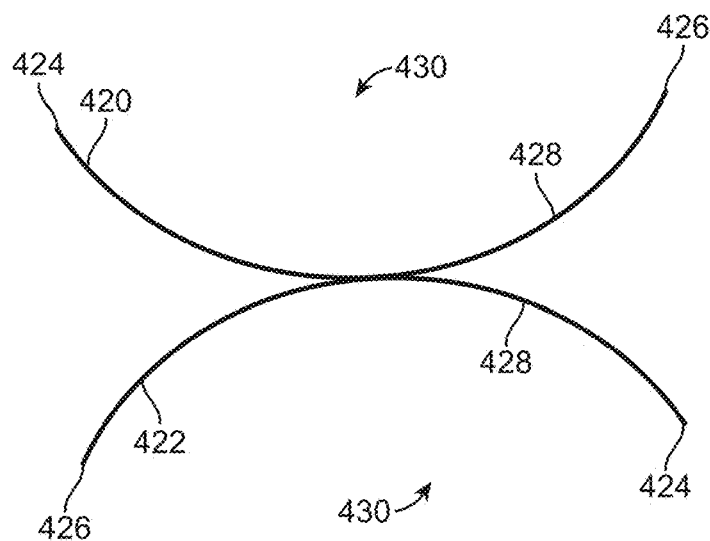
FIG. 18 is a section view of one embodiment of a deployable tendril.

FIG. 18 depicts a section view of a tendril 402 taken along plane A-A shown in FIG. 17. As seen in FIG. 18, in some embodiments, each of the blades 420, 422 can have an arcuate cross-section which can allow flexing and/or bending in one direction perpendicular to the longitudinal axis of the blade 420, 422. Specifically, each of the blades 420, 422 can comprise a first end 424, a second end 426, and an arcuate member 428, also referred to herein as the arcuate component 428 extending between the first and second ends 424, 426. In some embodiments, the arcuate component 428 can open to define a partially enclosed volume 430. In some embodiments, when the tendrils 402 are deployed, the first and second blades 420, 422 can be positioned adjacent to and/or abutting each other such that the arcuate component 428 of the first blade 420 opens in a direction different than, and in some embodiments a direction opposite to the direction in which the arcuate component 428 of the second blade 422 opens. Thus, in some embodiments, the first blade 420 and/or the arcuate member 428 of the first blade 420 is oriented in a first direction and the second blade 422 and/or the arcuate member 428 of the second blade is oriented in a second direction.

The skin anchor 400 can include an annular ring 432. In some embodiments, the annular ring 432 can be located intermediate, and in some embodiments equidistant, between the inward ring 412 and the outward ring 414. In some embodiments, the annular ring 432 can comprise a first channel 434 and a second channel 436. In some embodiments, the first channel 434 can receive the first blade 420 and can redirect the first blade 420 so as to change the orientation of the first blade 420 with respect to the stator 404. Similarly, in some embodiments, the second channel 436 can receive the second blade 422 and can redirect the second blade 422 so as to change the orientation of the second blade 422 with respect to the stator 404.

Figure 19:
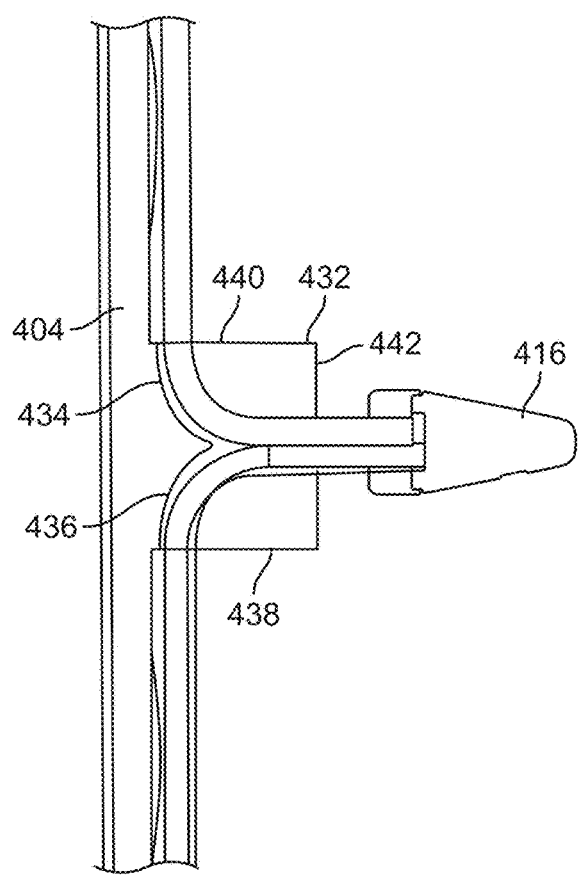
FIG. 19 is a section view of one embodiment of an annular ring of a skin anchor.

A section view of the annular ring 432 is shown in FIG. 19. The annular ring 432 includes an inward portion 438 relatively more proximate to the inward ring 412 than to the outward ring 414, an outward portion 440 relatively more proximate to the outward ring 414 than to the inward ring 412, and a front face 442. The first channel 434 enters into the outward portion 440 of the annular ring 432 and curves to exit the front face 442 of the annular ring 432. In some embodiments, this curve of the first channel 434 can be a 90 degree curve. The second channel 436 enters into the inward portion 438 of the annular ring 432 and curves to exit the front face 442 of the annular ring 432. In some embodiments, this curve of the first channel 434 can be a 90 degree curve. In some embodiments, the first channel 434 and the second channel 436 can be parallel and/or approximately parallel when exiting the front face 442 of the annular ring 432, and in some embodiments, the first channel 434 and the second channel 436 can merge into a single channel before exiting the front face 442 of the annular ring 432. In some embodiments, the first and second blades 420, 422 can exit the annular ring 432 in a radial orientation, and in some embodiments, the first blade 420 can contact the second blade 422 when or after the first and second blades 420, 422 exit the annular ring 432.

In some embodiments, the skin anchor 400 can further include tug 444 that can connect, either directly or indirectly, to one or both of the inward and outer rings 412, 414 via a plurality of tendons 446. In some embodiments, the skin anchor 400 can comprise 4 tendons that can be, for example, equally spaced around the circumference and/or perimeter of the stator 404. The tendons 446 can comprise a variety of shapes and sizes and can be made from a variety of materials. In some embodiments, the tendons 446 can be made of the same material as the tug 444, and in some embodiments, the tendons 446 can be made from a different material than the tug 444. In some embodiments, the tendons 446 can comprise thin elongate members made of a flexible material.

In some embodiments, the tug 444 can be connected to both the inward and outer rings 412, 414 such that movement of the tug 444 results in equal and opposite movement of the inward and outer rings 412, 414. In some embodiments, for example, when the tug 444 is moved from the first position shown in FIG. 16 towards the second position shown in FIG. 17, the tendons 446 are tightened and the inward and outer rings 412, 414 are equally and oppositely displaced towards the annular ring 432. In some embodiments, this equal and opposite movement of the inward and outer rings 412, 414 can be achieved via the tendon. In some embodiments, for example, a first end of each tendon 446 is fixed to the outward ring 414. The tendon 446 passes along the stator 404, through an aperture 450 in the annular ring 432, through an aperture 451 in the inward ring 412, and to a base flange 452 of the stator 404. The tendon 446 wraps around a shaft in the base flange 452 and returns along the stator 404 towards the tug 444. The tendon 446 passes again the aperture 451 in the inward ring 412 and connects to the inward ring 412. The tendon 446 continues along the stator 404 towards the tug 444 and passes through the aperture 450 in the annular ring 432, through an aperture in the outer ring 414, and finally connects to the tug 444. In some embodiments, this routing of the tendon 446 and connection of the tendon 446 to the inward and outer rings 412, 414 and the tug 444 results in the equal and opposite movement of the inward and outer rings 412, 414 towards the annular ring 432 when the tug 444 is moved from the position shown in FIG. 16 to the position shown in FIG. 17.

In some embodiments, and as the inward and outer rings 412, 414 approach the annular ring 432, the inward and outer rings 412, 414 contact the feature 406 and cam against the features 406 such that the features are pushed into the exterior of the driveline 27 to secure the position of the driveline 26 with respect to the stator 40. In some embodiments, simultaneous with the increased engagement of the features 406 and the driveline 26, the features 406 engage with the inward and outer rings 412, 414 to secure the position of the inward and outer rings 412, 414 with respect to the stator. In some embodiments, one or both of the inward and outer rings 412, 414 can further include one or several features such as one or several ridges or grooves that can positively engage with a portion of the features 406 such as, for example, an end of the features 406 to positively secure the position of each of the inward and outer rings 412, 414 with respect to the stator 404 and to secure the tendrils 402 in the deployed position. In some embodiments, after the inner and outer rings 412, 414 have been moved so that the tendrils 402 are in a deployed configuration, the tendons 446 can be severed and the tug 444 and portions of the tendons 446 connected to the tug 444 can be removed from the patient's body.

With reference now to FIG. 20, a flowchart illustrating one embodiment of a process 500 for affixing a driveline to a portion of skin is shown. In some embodiments, this process can be performed, for example, using any of the herein disclosed skin anchors. The process 500 begins at block 502, wherein the implantable blood pump 14, the external controller 20, the driveline 26, and the skin anchor are provided. The process 500 then proceeds to block 504, wherein the implantable blood pump 14 is implanted. In some embodiments, this can include, for example, connecting the implantable blood pump 14 to desired tissue and/or to one or several desired organs.

At block 506, a driveline path through the patient's body is created. In some embodiments, this can include the routing of the driveline 26 through the patient's body such that the driveline 26 exits the patient's body at a desired location and/or passes one or several desired bones, tissues, or organs. In some embodiments, the creation of the driveline path can be performed via the displacement of a tunneling bullet attached to the driveline through a portion of the patient's body.

At block 508, a port 34 is created through the patient's skin. In some embodiments, this can include the incising of the patient's skin and/or tissue to create a port and/or partially closing a pre-existing incision to create the port 34. In some embodiments, and as part of creating the port 34, the driveline 26 can be passed through the port 34 such that a portion of the driveline 26 is inside of the patient's body and another portion of the driveline is outside of the patient's body.

At block 510, the skin anchor is attached to the driveline 26. In some embodiments, this can include receiving the driveline in the driveline capture portion 264 of the driveline 26 and fixing the position of the driveline 26 with respect to the driveline capture portion 264. This can specifically include receiving the driveline with the driveline receiver 268 of the skin anchor and engaging the driveline 26 with the driveline anchor 270 to fix the position of the driveline 26 with respect to the driveline receiver 268. In some embodiments, this can include inserting the driveline 26 through an aperture of the skin anchor and/or connecting portions of the skin anchor around the driveline 26.

At block 512, the skin anchor is connected to, and/or fixed to the skin, and specifically to a portion of skin that can be, for example, proximate to the port 34 or surrounding the port 34. In some embodiments, this can include removing the tunneling bullet from the driveline 26, positioning the force distribution portion proximate to the skin or portion of skin, and/or deploying one or several tendrils. In some embodiments fixing the skin anchor to a portion of skin proximate to a port through which the driveline exits the patient's body via a force distribution portion can include: positioning the force distribution portion proximate to the portion of skin and moving the plurality of tendrils to a deployed position. In some embodiments, moving the plurality of radially extendable tendrils to a deployed position can include redirecting first and second blades through an annular ring of a stator from a longitudinal orientation to a radial orientation by centrally displacing a first slider ring connected to the first blade and a second slider ring connected to the second blade.

At block 514, the external controller 20 is electrically connected to the implantable pump 14 via the driveline 26. In some embodiments, this can include the providing of power to the implantable pump 14 via the driveline 26 and/or the providing of control signals to the implantable pump 14 via the driveline.

Figure 21:
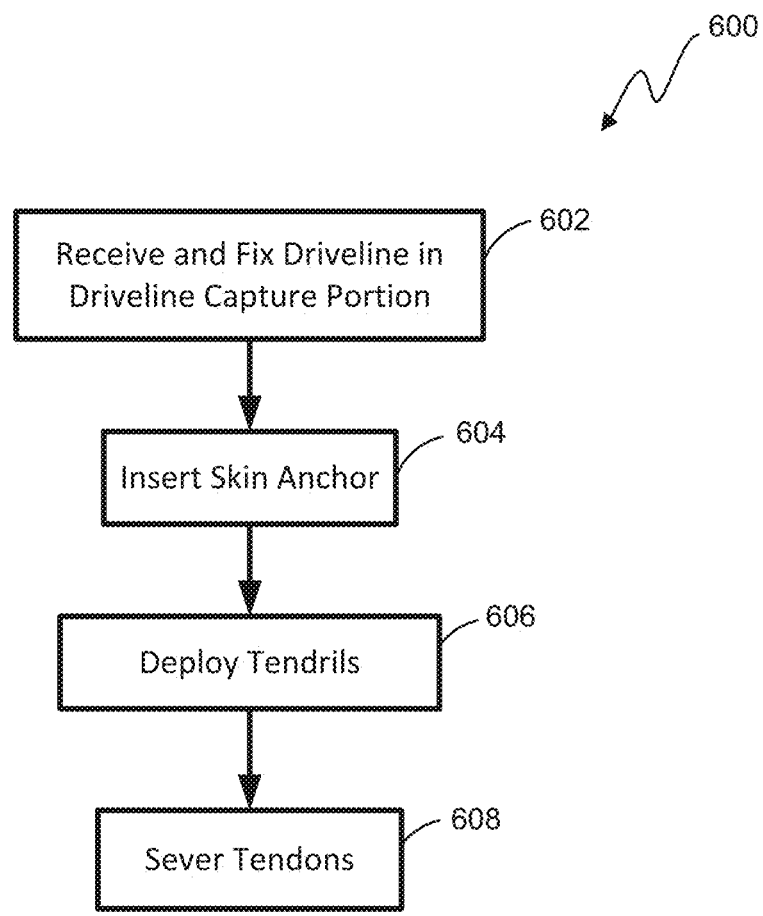
FIG. 21 is a flowchart illustrating one embodiment of a process for implanting the skin anchor.

With reference now to FIG. 21, a flowchart illustrating one embodiment of a process 600 for implanting the skin anchor 400 is shown. The process 600 can be performed as a part of, or in the place of blocks 510 and 512 of FIG. 20. The process 600 begins at block 602, wherein the driveline 26 is received within the driveline capture portion 254 of the skin anchor 400. The process 600 then proceeds to block 604, wherein the skin anchor 400 is inserted into the patient's body. In some embodiments, the skin anchor 400 is inserted into the patient's body such that the flukes 416 of the tendrils 402 tendrils are subdermal.

After the skin anchor 400 has been inserted into the patient's body, the tendrils 402 are deployed. In some embodiments, the tendrils 402 can be deployed by moving the tug 444 from a first position to a second position. In some embodiments, movement of the tug 444 from the first position to the second position causes the inward and outer rings 412, 414 to move towards the annular ring 432. In some embodiments, the inward and outer rings 412, 414 engage with the features 406 of the driveline capture portion 254, which features 406 secure the position of the outer rings 412, 414 and engage with the driveline 26 to secure the position of the driveline 26 relative to the skin anchor 400.

After the tendrils 402 are deployed, the process 600 proceeds to block 608 wherein the tendons 446 coupling the tug 444 and the inward and outer rings 412, 414 are severed. In some embodiments, this severing of the tendons 446 can be performed using a cutting tool such as a knife, a scalpel, or scissors, and in some embodiments, the tendons 446 can be severed via the application of a sufficiently large force to the tug 444 to cause the tendons to break. In some embodiments, step 608 can further include trimming the stator to a desired length.

In the preceding description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A skin anchor for securing a percutaneous driveline to a portion of skin, the driveline connecting an external controller or power source to an implantable blood pump, the skin anchor comprising:
   a driveline capture portion configured to receive the driveline and fix a position of the driveline with respect to the driveline capture portion, wherein the driveline capture portion comprises:
      a driveline receiver configured to receive the driveline; and
      a driveline anchor configured to engage the driveline to fix the position of the driveline with respect to the driveline receiver; and
   a force distribution portion extending from the driveline and configured to engage a portion of the skin and fix a position of the force distribution portion with respect to the portion of the skin so as to secure the force distribution portion directly to the skin.

2. The skin anchor of claim 1, wherein the force distribution portion comprises an enlarged member having a diameter larger than a diameter of the driveline and radially extending from the driveline when the driveline is received within the driveline capture portion.

3. The skin anchor of claim 1, wherein the force distribution portion comprises a plurality of radially extendable tendrils.

4. The skin anchor of claim 3, wherein each of the radially extendable tendrils comprises a first arcuate component oriented in a first direction and a second arcuate component oriented in a second direction, wherein the first direction is opposite the second direction, wherein each of the radially extendable tendrils comprises the first arcuate component contacting the second arcuate component.

5. A system for securing a driveline to a portion of skin via a skin anchor, the driveline electrically connecting an external controller and an implantable blood pump, the system comprising:
   an implantable blood pump comprising a rotor and a stator;

an external controller configured to power the implantable blood pump and provide a control signal to the implantable blood pump;
a percutaneous driveline electrically connecting the implantable blood pump and the external controller, wherein the percutaneous driveline has a diameter; and
a skin anchor comprising:
  a driveline capture portion configured to receive the driveline and fix a position of the driveline with respect to the driveline capture portion; and
  a force distribution portion extending from the driveline and configured to engage a portion of the skin and fix a position of the force distribution portion with respect to the portion of the skin so as to secure the force distribution portion directly to the skin.

6. The system of claim 5, wherein the force distribution portion comprises an enlarged member, having a diameter larger than a diameter of the driveline, and wherein the enlarged member radially extends from the driveline when the driveline is received within the driveline capture portion.

7. The system of claim 5, wherein the force distribution portion comprises a plurality of radially deployable tendrils.

8. The system of claim 7, wherein each of the radially deployable tendrils comprises a first blade oriented in a first direction and a second blade oriented in a second direction, wherein each of the first and second blades comprise a pair of ends and an arcuate component located between the pair of ends, wherein the first direction is opposite the second direction, and wherein the arcuate component of the first blade abuts the arcuate component of the second blade.

9. A method for affixing a driveline to a portion of skin, wherein the driveline electrically connects an external controller to an implantable blood pump, the method comprising:
  implanting the implantable blood pump in a patient's body;
  creating a driveline path through a patient's body;
  connecting the driveline to a skin anchor via a driveline capture portion configured to receive the driveline and fix a position of the driveline with respect to the driveline capture portion, wherein the driveline capture portion comprises:
    a driveline receiver configured to receive the driveline; and
    a driveline anchor configured to engage the driveline to fix the position of the driveline with respect to the driveline receiver;
  connecting the skin anchor to a portion of skin proximate to a port through which the driveline exits the patient's body via a force distribution portion extending from the driveline and configured to engage a portion of the skin so as to fix a position of the force distribution portion with respect to the portion of the skin and secure the force distribution portion directly to the skin; and
  electrically connecting the external controller and the implantable blood pump.

10. The method of claim 9, wherein the force distribution portion comprises an enlarged member radially extending from the driveline, and wherein connecting the skin anchor to the portion of skin proximate to the port through which the driveline exits the patient's body comprises subdermally positioning the force distribution adjacent to the portion of skin proximate to the port.

11. The method of claim 10, wherein the enlarged member has a diameter that is at least one of: larger than the port; or larger than a diameter of the driveline.

12. The method of claim 9, wherein connecting the skin anchor to a portion of skin proximate to a port through which the driveline exits the patient's body via a force distribution portion comprises: positioning the force distribution portion proximate to the portion of skin; and moving a plurality of radially extendable tendrils to a deployed position.

13. The method of claim 12, wherein moving the plurality of radially extendable tendrils to a deployed position comprises redirecting first and second arcuate members through an annular ring of a stator from a longitudinal orientation to a radial orientation by centrally displacing a first slider ring connected to the first arcuate members and a second slider ring connected to the second arcuate members.

14. The method of claim 13, wherein the first and second arcuate members exit the annular ring in the radial orientation, wherein the first arcuate member contacts the second arcuate member when the first and second arcuate members exit the annular ring.

15. The method of claim 14, wherein the first and second slider rings are centrally displaced by displacement of a tug connected to the first slider ring via a first tendon and connected to the second slider ring via a second tendon, wherein the first and second tendons connect to the first and second slider rings such that displacement of the tug causes equal displacement of the first and second slider rings.

* * * * *